US012704418B2

(12) United States Patent
Cornett et al.

(10) Patent No.: US 12,704,418 B2
(45) Date of Patent: Aug. 11, 2026

(54) SENSING ASSEMBLY

(71) Applicant: Analog Devices International Unlimited Company, Limerick (IE)

(72) Inventors: Jane Cornett, Reading, MA (US); Yi Yuan, Malden, MA (US); Baoxing Chen, Westford, MA (US); Ciaran Curtin, Ovens (IE)

(73) Assignee: Analog Devices International Unlimited Company, Limerick (IE)

(*) Notice: Subject to any disclaimer, the term of this patent is extended or adjusted under 35 U.S.C. 154(b) by 308 days.

(21) Appl. No.: 18/569,784

(22) PCT Filed: Jun. 14, 2022

(86) PCT No.: PCT/EP2022/066127
§ 371 (c)(1),
(2) Date: Dec. 13, 2023

(87) PCT Pub. No.: WO2022/263421
PCT Pub. Date: Dec. 22, 2022

(65) Prior Publication Data

US 2024/0272015 A1 Aug. 15, 2024

Related U.S. Application Data

(60) Provisional application No. 63/210,454, filed on Jun. 14, 2021.

(51) Int. Cl.
*G01K 13/20* (2021.01)
*A61B 5/01* (2006.01)
(Continued)

(52) U.S. Cl.
CPC ................ *G01K 13/20* (2021.01); *A61B 5/01* (2013.01); *G01K 1/026* (2013.01); *G01K 1/143* (2013.01)

(58) Field of Classification Search
CPC . G01K 13/20; G01K 1/43; A61B 5/01; A61B 2562/0271
(Continued)

(56) References Cited

U.S. PATENT DOCUMENTS

2016/0313193 A1 10/2016 Nakagawa et al.
2017/0276553 A1 9/2017 Nakagawa et al.
2020/0390336 A1* 12/2020 Mensch .................. A61B 5/01

FOREIGN PATENT DOCUMENTS

WO 2019126607 A1 6/2019
WO WO-2019133469 A1 * 7/2019 ............... A61B 5/01
WO WO-2020213437 A1 * 10/2020 ............. G01K 13/20

OTHER PUBLICATIONS

International Search Report and Written Opinion for International Patent Application No. PCT/EP2022/066127, mailed Nov. 21, 2022 (15 pages).

* cited by examiner

*Primary Examiner* — Mirellys Jagan
(74) *Attorney, Agent, or Firm* — ArentFox Schiff LLP

(57) ABSTRACT

The present disclosure provides a core temperature sensing assembly for measuring a core temperature of an object when positioned on a surface of the object. The sensing assembly uses a heat flux sensor in the form of a thermoelectric generator. The thermoelectric generator is provided as part of an integrated circuit. Alternatively or additionally, the sensing assembly uses the thermoelectric generator to actively heat or cool the object. Alternatively or additionally, the sensing assembly comprises a second heat flux sensor in the form of a thermoelectric generator, the first and second heat flux sensors having different thermal resistances determined by the configuration of the thermocouples.

23 Claims, 10 Drawing Sheets

(51) Int. Cl.
*G01K 1/02* (2021.01)
*G01K 1/143* (2021.01)
*G01K 17/00* (2006.01)

(58) Field of Classification Search
USPC .......................................... 374/29, 208, 113
See application file for complete search history.

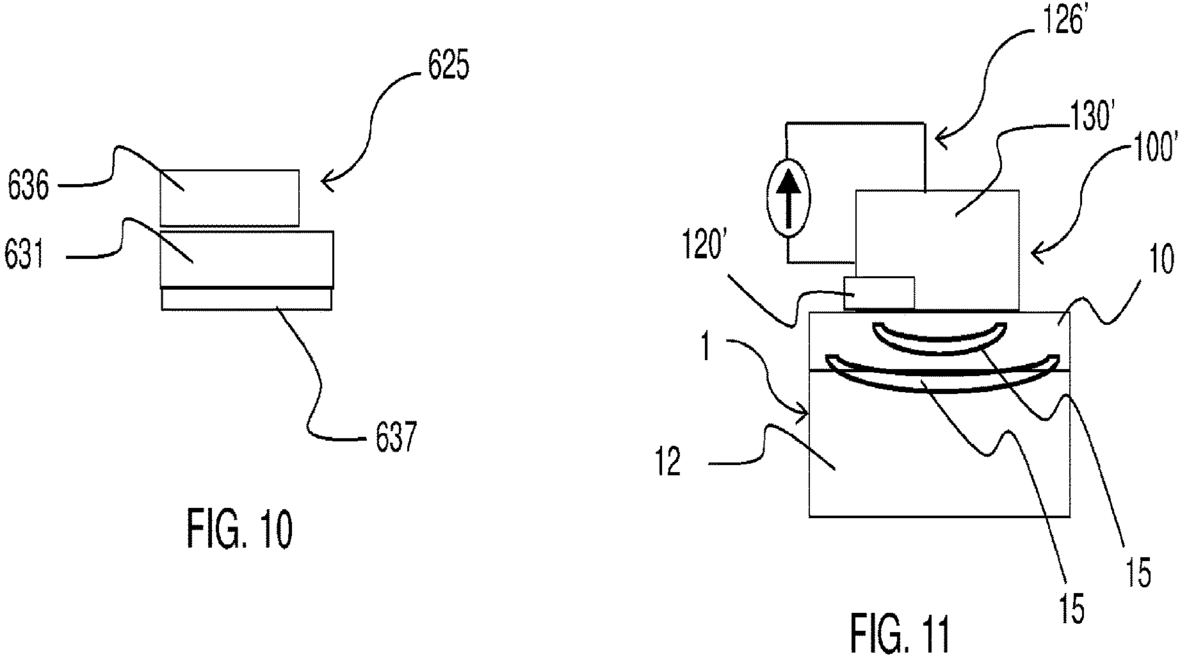
FIG. 10
FIG. 11
FIG. 12
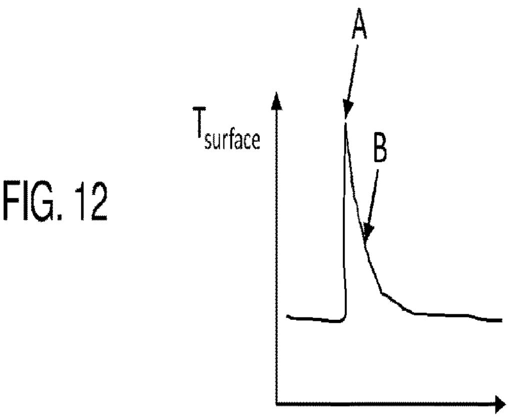

SENSING ASSEMBLY

CROSS-REFERENCE TO RELATED APPLICATIONS

This application is a 35 U.S.C. § 371 National Stage Application of International Patent Application No. PCT/EP2022/066127, filed on Jun. 14, 2022, which application claims the benefit of and priority to U.S. Provisional Patent Application No. 63/210,454, filed Jun. 14, 2021, the contents of each of which applications are hereby incorporated by reference herein in their entireties.

FIELD OF THE DISCLOSURE

This disclosure relates to sensing assemblies, particularly core temperature sensing assemblies for determining a core temperature of an object, and systems and methods for determining a core temperature of an object.

BACKGROUND

Various systems are known for determining or estimating the core temperature of an object by measuring parameters at a surface of the object. Existing core temperature measurement systems include systems incorporating heat flux sensors and temperature sensors, which sensors are placed on an outer surface of the object and are used to estimate or measure the temperature below the surface (the "core temperature" or $T_{core}$). These systems are used, for example, in determining the core body temperature of a human or animal or monitoring the temperature of an internal part of a device (e.g. a battery).

Many systems which use heat flux-based sensors suffer from drawbacks. One method of determining core temperature uses the "zero heat flux" principle. This is an active sensing technique whereby a heater is placed in series with a heat flux sensor and is used to heat the surface. The core temperature is known, and is equal to the surface temperature ($T_{surface}$), when the net heat flux q=0. This can provide an accurate measurement of the core temperature but requires power input for the heating element. This can also make the devices bulky and cumbersome, as the heating element increases the footprint of the device and requires a DC power supply, which is not suited to a number of applications.

Passive-based core temperature sensor systems include "single heat flux" and "dual heat flux" systems. A single heat fluxsystem may use one sensor device having two temperature sensors separated by a material of known thermal resistance. The temperature measurements from the two temperature sensors are used to estimate a core temperature. In such systems employing two temperature sensors, these sensors can be difficult to miniaturize due to the use of bulk materials of precise thermal resistance between the two temperature sensors. Moreover, these can also have a lower sensitivity and be more susceptible to environmental effects. More generally, single heat flux systems can be less accurate than the other heat flux measurements, as it requires an estimate of the thermal resistance between the core and the surface of the object ($R_{object}$) and knowledge of the thermal resistance between the two temperature sensors, which can be difficult to accurately ascertain. Moreover, the dual heat flux method uses two sensor devices each having two sensors having a structure similar to that of the single heat flux devices. By using two sensor devices, the thermal resistance $R_{object}$ may not need to be known and can also be determined. This allows for a more accurate calculation of the core temperature.

Some systems may use a heat flux sensor instead of one of the temperature sensors in the sensor device(s). However, core temperature sensors based on heat flux detection can still suffer from a number of drawbacks due to limitations of the heat flux sensors. These include limited accuracy or sensitivity which in turn limits uses. For example, the use in measuring or monitoring core temperature in certain applications such as monitoring of core body temperature may be limited to particular implementations or locations of the body. For these and other uses, the systems can be too bulky or those that are smaller suffer from lower sensitivity or accuracy.

Thermoelectric generators (TEGs) may be used for measuring heat flux. However, existing heat flux sensing devices using thermoelectric generators still suffer from these drawbacks, including being bulky and lacking the accuracy and performance required for all sensing applications. This is because heat flux sensors are typically manufactured from discrete thermoelectric elements and there are inherent limits to miniaturization without sacrificing sensitivity or accuracy performance. For example, thermoelectric generators formed as laminate structures with integrated discrete or bulk thermoelectric elements, limiting miniaturization without sacrificing the sensitivity and accuracy of the sensors.

SUMMARY OF THE DISCLOSURE

The present disclosure provides a core temperature sensing assembly for measuring a core temperature of an object when positioned on a surface of the object. The sensing assembly uses a heat flux sensor in the form of a thermoelectric generator. The thermoelectric generator is provided as part of an integrated circuit. Alternatively or additionally, the sensing assembly uses the thermoelectric generator to actively heat or cool the object. Alternatively or additionally, the sensing assembly comprises a second heat flux sensor in the form of a thermoelectric generator, the first and second heat flux sensors having different thermal resistances determined by the configuration of the thermocouples.

In certain embodiments, a core temperature sensing assembly for determining a core temperature of an object when positioned on a surface of the object is disclosed which comprises a first sensor device for placement at a first surface location, the first sensor device comprising: a first heat flux sensor configured to measure heat flux at the first surface location and output a first heat flux signal relating to the measured heat flux; and a first temperature sensor configured to measure a temperature at the first surface location and output a first temperature signal relating to the measured temperature, wherein the first heat flux sensor is a first thermoelectric generator; and wherein the sensing assembly comprises a first integrated circuit comprising the first thermoelectric generator.

In certain embodiments, a core temperature sensing assembly for determining a core temperature of an object when positioned on a surface of the object is disclosed which comprises a first sensor device for placement at a first surface location, the first sensor device comprising: a first heat flux sensor configured to measure heat flux at the first surface location and output a first heat flux signal relating to the measured heat flux; and a first temperature sensor configured to measure temperature at the first surface location and output a first temperature signal relating to the measured temperature, wherein the first heat flux sensor comprises a first thermoelectric generator configured to measure heat flux at the first surface location; and wherein the sensing assembly is further configured to cause the first thermoelectric generator of the first sensor device to actively heat or cool the first surface location.

In certain embodiments, a core temperature sensing assembly for determining a core temperature of an object when positioned on a surface of the object is disclosed which may comprise:

- a first sensor device for placement at a first surface location, the first sensor device comprising:
  - a first heat flux sensor configured to measure heat flux at the first surface location and output a first heat flux signal relating to the measured heat flux; and
  - a first temperature sensor configured to measure temperature at the first surface location and output a first temperature signal relating to the measured temperature; and
- a second sensor device for placement at a second surface location, the second sensor device comprising:
  - a second heat flux sensor configured to measure heat flux at the second surface location and output a second heat flux signal relating to the measured heat flux and
  - a second temperature sensor configured to measure temperature at the second surface location and output a second temperature signal relating to the measured temperature,
- wherein the first heat flux sensor comprises a first thermoelectric generator configured to measure heat flux at the first surface location and the second heat flux sensor comprises a second thermoelectric generator configured to measure heat flux at the second surface location; and
- wherein the first thermoelectric generator comprises at least one first thermocouple having a first thermocouple configuration and the second thermoelectric generator comprises at least one second thermocouple having a second thermocouple configuration, the first and second thermocouple configurations being different such that the thermal resistance of the first thermoelectric generator is different to the second thermoelectric generator.

In certain embodiments, a method for determining a core temperature of an object is disclosed which may comprise: receiving a first heat flux signal from a first heat flux sensor of a first sensor device relating to a measured first heat flux and receiving a first temperature signal from a first temperature sensor of the first sensor device relating to a measured first temperature, the first heat flux sensor being a first thermoelectric generator and the first sensor device comprising a first integrated circuit comprising the first thermoelectric generator; and calculating a core temperature based on the measured heat flux from the first heat flux signal and the measured temperature from the first temperature signal.

BRIEF DESCRIPTION OF THE DRAWINGS

The present invention will now be described in more detail with reference to the accompanying drawings, which are not intended to be limiting:

FIG. 10 provides a schematic view of an integrated circuit for use in embodiments;

FIG. 11 provides a schematic cross-sectional view of a sensing assembly according to an embodiment;

FIG. 12 provides a graph depicting a heating profile using a sensing assembly according to an embodiment;

DETAILED DESCRIPTION

Figure 1:
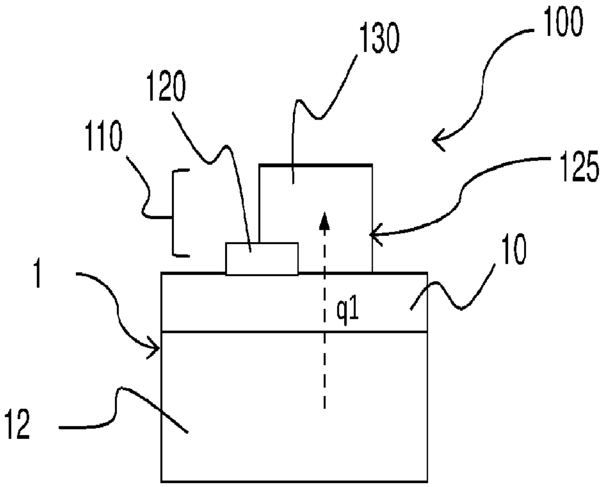
FIG. 1 provides a schematic cross-sectional view of a sensing assembly according to an embodiment.

Systems for determining or estimating the core temperature of an object can determine heat flux and temperature at the surface of the object using sensors placed on the surface. For example, in the case of core body temperature, a sensor can be placed on the skin of the subject (e.g. a person or animal) and be used to determine the temperature beneath the skin. In devices, a similar principle can be employed to measure core temperature of either an inner part of the device object or the temperature of the contents of the device or object.

As discussed above, "single heat flux" and "dual heat flux" systems are examples of passive-based sensing systems which can be used to determine core temperature. These both determine the core temperature of an object by measuring heat flux using one or two sensor devices, which sensor devices each comprise either two temperature sensors or a heat flux sensor and a temperature sensor. These heat flux measuring systems have the advantage of being non-invasive; however, typical systems have a large footprint and, if scaled down, would lack the accuracy or sensitivity for a number uses. For example, in surgical or clinical settings (such as monitoring of a patient's core body temperature during surgery) alternative measurement systems are typically employed. These can include invasive sensing technologies where esophageal, bladder and rectal temperatures are monitored. Alternatively, the sensor measurement site may be limited to a single specific body location. Therefore, there is a desire to provide an improved sensing assembly.

Moreover, systems relying on heat flux determination methods often need to trade off between sensitivity of the heat flux sensors and the size and cost of the devices. In systems relying on two temperature sensors in each sensor device, there are also limitations to sensor miniaturization resulting from the need to know the precise thermal resistance of a bulk material between the two temperature sensors and these systems have a high response time and lower sensitivity, and are more susceptible to environmental conditions. In systems using heat flux sensors, these often rely on the use of heat flux sensors manufactured from discrete device components, which limits the sensitivity, accuracy and size reductions are difficult without sacrificing performance.

Certain embodiments of the present disclosure provide a core temperature sensing assembly with a first sensor device comprising a thermoelectric generator as a heat flux sensor and a temperature sensor. The thermoelectric generator can be provided as part of an integrated circuit.

Thermoelectric generators ("TEGs"), (also referred to as Seebeck generators or thermoelectric devices/generators) convert heat (e.g., thermal energy) into electric energy (e.g. a voltage output) through a phenomenon known as the "Seebeck effect". A temperature gradient is formed by contacting one side of the TEG with a hotter or colder surface. This temperature gradient results in the diffusion of charge carriers in a semiconductor material in the device. The flow of charge carriers between the hot and cold sides or regions in turn creates a voltage difference. In embodiments, this semiconductor material can be in the form of at least one thermoelectric element, which may form a thermocouple where there are plural semiconductor materials, for example. Plural thermocouples can form a thermopile. In embodiments, the thermoelectric generator can be placed onto the surface causing one side of the thermoelectric generator to be hotter than the other and generate a voltage output.

Use of thermoelectric generators as heat flux sensors in core temperature sensing assemblies can provide a more accurate and more sensitive means by which to determine heat flux and advantageously avoids the drawbacks of the sensor devices in which the heat flux is determined by the use of a bulk material of precise thermal resistance between two temperature sensors. Instead, this is more consistent and can be more accurately provided or determined during manufacture of the integrated circuit (e.g. using semiconductor processing methods). Further, use of the thermoelectric generators eliminates one of the temperature sensors, for example the temperature sensor on the top (ambient) side of the bulk material, which otherwise can be affected by environmental factors (and thus reduce the accuracy of the reading). Thermoelectric generators in embodiments can be solid state devices and therefore can provide a robust means of measuring heat flux.

The thermoelectric generator may be provided as part of an integrated circuit. Alternatively or additionally, the sensing assembly uses the thermoelectric generator to actively heat or cool the object. Alternatively or additionally, the sensing assembly comprises a second heat flux sensor in the form of a thermoelectric generator, the first and second heat flux sensors having different thermal resistances.

Embodiments of core temperature sensing assemblies in which the thermoelectric generator is provided as part of an integrated circuit may provide high sensitivity and accuracy. For example, in at least some embodiments, integrated circuitry allows for an increased density of thermocouples in the device, as compared to heat flux sensors manufactured from discrete device components. Existing sensing assemblies using bulk-packaged thermoelectric generators are limited in terms of sensitivity and accuracy relative to size. In embodiments, an increased number or thermocouples can improve the sensitivity of the devices in embodiments. To date it has also been difficult to scale down the size of thermoelectric generators for new applications. For example, scaling down the size of the thermoelectric generator typically would have reduced sensitivity and increased manufacturing costs. The configurations of the existing thermoelectric generators used in this particular field also limit this reduction in size.

In certain embodiments, the temperature sensors used in the embodiments disclosed herein may be an RTD temperature sensor, a thermocouple temperature sensor, a thermistor temperature sensor or an integrated silicon-based temperature sensor (e.g. ADT7422 or MAX30208 provided by Analog Devices Inc.).

In embodiments, measurements from the temperature sensor(s) and heat flux sensor(s) of embodiments of the assemblies disclosed herein are output in the form of a signal. As such, the output signal relates to corresponding measured parameters. This signal can be a raw voltage or data, or a processed signal. It will be appreciated that references to using the signal (e.g. in a calculation) mean using the data transmitted by the signal (i.e. the corresponding measurement information).

In certain embodiments, the core temperature sensing assembly may use a single heat flux method for determining core temperature ($T_{core}$). In such embodiments, the core temperature sensing assembly may comprise a single sensor device (e.g. only) and use the first heat flux ($q_1$) and first temperature ($T_1$), which can be the temperature at the surface of the device or at a position offset from the surface (e.g. behind the thermoelectric generator). For example, in certain embodiments, the core temperature ($T_{core}$) can be calculated as set out in equation 1:

$$T_{core} = T_1 + q_1 * R_{object} \quad \text{[equation 1]}$$

where $R_{object}$ is the thermal resistance from the surface of the object to the core of the object. $R_{object}$ can be estimated to provide the $T_{core}$ value. This can be estimated based on any known method in the art, and may be calibrated to each object and/or sensing assembly. The equations listed herein are provided as a simplified and generalized indication of how parameters such as $T_{core}$ can be calculated in theory. The skilled person would appreciate that in some practical implementations that the situation may be more complex, for example adjustments or further processing.

Without wishing to be bound by theory, in some embodiments, the accuracy of the core temperature calculation can be improved by the use of a thermoelectric generator in an integrated circuit as this improves the sensitivity and accuracy of the measurements by improving the accuracy and sensitivity of the $q_1$ value for the reasons mentioned above. This means that, in embodiments, the use of an integrated circuit thermoelectric generator can obviate the need for multiple heat flux sensors (e.g. based on the dual heat flux method), for example when used in applications where $R_{object}$ is known and remains relatively constant.

In some embodiments, the core temperature sensing assembly may comprise two sensor devices. For example, a first sensor device for placement at/located at a first surface location of an object and a second sensor device for placement at/located at a second surface location of an object. The second heat flux sensor can comprise a second heat flux sensor configured to measure heat flux at the second surface location and output a second heat flux signal relating to the measured heat flux and a second temperature sensor configured to measure temperature at the second surface location and output a second temperature signal relating to the measured temperature. Measurement at the surface location can include measurement on the surface of the device or at a position offset from the surface (e.g. behind the thermoelectric generator). The first heat flux ($q_1$), the first temperature ($T_1$), the second heat flux ($q_2$) and the second temperature ($T_2$) may be used to calculate the core temperature. The two sensor devices are located at two different surface locations. In embodiments, these may be provided in a single device, for example as an assembly in a single housing. In alternative embodiments, these may be provided as separate devices within the same assembly (e.g. in different housings). In certain embodiments, the first and second sensor device may be separated by a thermal gap. In some embodiments, the gap may be provided by a thermal barrier.

In certain embodiments using two sensor devices, a dual heat flux method is used to determine core temperature ($T_{core}$). In such embodiments, the first thermoelectric generator and the second thermoelectric generator have different thermal resistances (or thermal conductivities). That is, they have a first and second thermal resistance, respectively, and the first and second thermal resistances are different. Thermal resistance or thermal conductivity relates to the ability of the thermoelectric generator (or the materials forming the thermoelectric generator) to conduct heat (units of W/m° K).

In dual heat flux methods which rely on measurements from two sensor devices made up of two temperature sensors separated by a known thermal resistance, each device has a surface temperature sensor (generating temperature readings of $T_{surface1}$ (first sensor device) and $T_{surface2}$ (second sensor device)) and a temperature sensor spaced apart from the surface temperature sensor by a body of known thermal resistance (generating temperature readings of $T_{top1}$ (first sensor device) and $T_{top2}$ (second sensor device)). The heat flux ($q_1$ (first sensor device), $q_2$ (second sensor device)) for each sensor device is calculated as set out in equations 2 and 3 respectively:

$$q_1 = \frac{T_{surface1} - T_{top1}}{Rsensor1} \quad \text{[equation 2]}$$

$$q_2 = \frac{T_{surface2} - T_{top2}}{Rsensor2} \quad \text{[equation 3]}$$

where $R_{sensor}$ is the thermal resistance of the material separating the two temperature sensors in each device. Thus, $R_{sensor1}$ is the thermal resistance between the first and second temperature sensors of the first sensor device and $R_{sensor2}$ is the thermal resistance between the first and second temperature sensors of the second sensor device. By having different thermal resistances in each of the sensor devices, the thermal resistance between the core and surface of the object does not need to be known.

The temperature measurements and calculated heat flux values can be used to calculate the core temperature ($T_{core}$) using equation 4:

$$T_{core} = \frac{T_{surface1} q_2 - T_{surface2} q_1}{q_2 - q_1} \quad \text{[equation 4]}$$

And to calculate $R_{object}$ (the thermal resistance from the surface of the object to the core) using equation 5:

$$R_{object} = \frac{T_{core} - T_{surface1}}{q_1} \text{ or } R_{object} = \frac{T_{core} - T_{surface2}}{q_2} \quad \text{[equation 5]}$$

However, as noted above, alongside device limitations, using two temperature sensors in each sensor device can lead to inaccuracies due to the environmental impacts on the ambient temperature sensor.

In certain embodiments, the use of a thermoelectric generator as a heat flux sensor provides a more accurate measurement system by allowing for removal of the second temperature sensor, which can otherwise be subject to environmental effects. This reduces or eliminates the inaccuracies that can arise in equations 2 and 3. In certain embodiments, the core temperature ($T_{core}$) and optionally also $R_{object}$ can be calculated using equation 6 and equation 7, respectively, based on the measured heat flux from the first heat flux sensor and measured heat flux from the second heat flux sensor:

$$T_{core} = \frac{T_1 q_2 - T_2 q_1}{q_2 - q_1} \quad \text{[equation 6]}$$

$$R_{object} = \frac{T_{core} - T_1}{q_1} \text{ or } R_{object} = \frac{T_{core} - T_2}{q_2} \quad \text{[equation 7]}$$

where $q_1$ is the first heat flux measured by the first heat flux sensor (i.e. the first thermoelectric generator), $T_1$ is the first temperature measured by the first temperature sensor, $q_2$ is the second heat flux measured by the second heat flux sensor (i.e. the second thermoelectric generator) and $T_2$ is the second temperature measured by the second temperature sensor.

As noted above, in certain embodiments, the thermoelectric generator(s) can be provided in an integrated circuit. By this it is meant that it is provided as a monolithic chip or integrated circuit die, such as an integrated wafer-level chip-scale package. In certain embodiments, this may be a silicon-based integrated circuit, such as an integrated circuit in which the substrate comprises silicon or consists of silicon. In certain embodiments, this may be an integrated circuit chip manufactured using a semiconductor device fabrication method. Existing thermoelectric generators used in heat flux measurements suffer from a number of drawbacks due to reliance on forming the thermoelectric generators from discrete individual devices as, e.g. a laminated bulk package. Compared to prior art thermoelectric generators used in the field which are limited to e.g. <5 thermocouples/mm$^2$, the use of integrated circuits enables the incorporation of at least 20 thermocouples/mm$^2$, at least 30 thermocouples/mm$^2$, or even at least 40 thermocouples/mm$^2$. Embodiments in which each thermoelectric generator in the assembly is provided as an integrated circuit have been found to obviate these issues and can provide a significant improvement in accuracy and sensitivity relative to size, as discussed above. These can be provided on a much smaller scale, without sacrificing performance. Examples of thermoelectric generators provided in an integrated circuit that can be used in certain embodiments are disclosed in US 2016/064637 A1, which is incorporated herein by reference.

Where the sensing assembly comprises a plurality of thermoelectric generators (such as a first thermoelectric generator as part of a first sensor device and a second thermoelectric generator as part of a second sensor device), these can be provided as part of a single integrated circuit (e.g. both on a single substrate) or may be provided on separate integrated circuits. Thus, references to first and second integrated circuits can refer to parts of the same integrated circuit (i.e. a single unitary integrated circuit with a single substrate) or may refer to separate integrated circuits.

In certain embodiments, the integrated circuit(s) may include a substrate (also referred to as a die or substrate layer) and a dielectric layer formed over the substrate. A plurality of thermoelectric elements may be disposed within the dielectric layer in the form of thermocouples. For example, in certain embodiments, there may be a plurality of p-type thermoelectric elements and a plurality of n-type thermoelectric elements. These may be electrically connected in series in an alternating fashion to form plural thermocouples (or a single thermopile). In certain embodiments, where thermoelectric elements are made from one p-type and one n-type thermoelectric element, the p-type thermoelectric elements can be $Bi_xSb_2$-x$Te_3$ and the n-type thermoelectric elements can be n-type $Bi_2Te_3$-x$Se_x$. In a non-limiting example, the dielectric layer can be a polyimide, silicon dioxide, or silicon nitride.

As noted above, in certain embodiments, a core temperature assembly can be used to determine core body temperature of a person or animal. In a non-limiting example, a method may comprise placing the core temperature assembly on the skin of a person or animal and using the device to measure the core body temperature of the person or animal. For example, the temperature of deep tissues, internal organs and cerebrum. The first sensor device can be at a first surface (e.g. skin) location and, if present, the second temperature device can be at a second, different surface (e.g. skin) location. Example locations for a person may include the head (such as the forehead, or ear), the core (e.g. chest, back (e.g. upper back), abdomen), the neck, the arm, the wrist or the foot. The signals output by the sensor device(s) can be used to calculate the core body temperature, for example as detailed above. For example, where present, a controller provided with the assembly or external to the assembly can receive and process the signals received from the sensor device(s) to determine the core body temperature based on the measured values. Core body temperature measurements have applicability in surgical or clinical settings, sports science, sleep monitoring, monitoring fertility and ovulation and early disease detection. These require a level of sensitivity and accuracy that is provided by embodiments of the invention.

The use of a dual heat flux method can, in embodiments, be advantageous in core body temperature measurements as a result of not needing to know $R_{object}$ (referred to as "$R_{body}$" in the context of core body temperature measurements). For example, single heat flux systems must estimate the resistance between the core and the temperature sensor ($R_{body}$). However, this is variable. In the context of core body temperature, this can vary based on the particular patient (e.g. body fat, bone density), location of the sensors, or other causes of variation. This limits the accuracy of single heat flux systems and the location at which the prior art sensor devices can be placed. For example, existing core body temperature sensors typically must be placed on regions where there is relatively little variability in $R_{body}$ (e.g. the skull). Embodiments which use dual heat flux methods can therefore provide improved core body temperature measurements, and can be used in other regions e.g. the chest or abdomen.

In an embodiment, the first temperature sensor may be provided to measure the temperature at or adjacent the first heat flux sensor and, if present, the second temperature sensor may be provided to measure the temperature at or adjacent the second heat flux sensor. The temperature sensor of each sensor device present in the assembly can be configured or arranged to be located at or adjacent the surface when the assembly is arranged on the surface (i.e. at the surface location), or may be spaced from the surface. Embodiments of the former may comprise the temperature sensor being located between the thermoelectric generator and the surface and may, for example, contact the surface. In these embodiments, the temperature detected by the temperature sensor may be referred to as $T_{surface}$. Embodiments of the latter may include each temperature sensor being located on or adjacent the thermoelectric generator but spaced from the surface. In these embodiments, the temperature detected by the temperature sensor may be referred to as $T_{top}$.

In certain embodiments, the first integrated circuit further comprises the first temperature sensor. In embodiments, the first temperature sensor may therefore be directly integrated into the integrated circuit with the first thermoelectric generator. Where a second sensor device is present, in embodiments additionally or alternatively, the second integrated circuit may further comprise the second temperature sensor. In embodiments, the second temperature sensor may therefore be directly integrated into the integrated circuit with the second thermoelectric generator. As noted above, the first and second integrated circuits may be provided as a single integrated circuit such that the sensing assembly comprises an integrated circuit comprising the first and second temperature sensors, where present. Without wishing to be bound by theory, such embodiments may provide a smaller overall footprint of the device without comprising on accuracy. By incorporating the temperature sensor in the integrated circuit, this can bring the temperature sensor into closer proximity with the thermoelectric generator, thereby reducing heat losses between the point at which heat flux is measured and where temperature is measured. This can ensure that accuracy of measurement is not loss by the integration. In certain embodiments, the temperature sensor may be in series with the heat flux sensor, which improves this accuracy further. That is, in embodiments, at least a part of the heat flux sensor can be located between the temperature sensor and the surface or at least a part of the temperature sensor can be located between the surface and the heat flux sensor (or a part thereof). For example, the first heat flux sensor may be configured to measure heat flux through the first temperature sensor (e.g. by taking into account heat flux through the sensor) and/or the second heat flux sensor may be configured to measure heat flux through the second temperature sensor.

In certain embodiments, the first integrated circuit may comprise a substrate and the first thermoelectric generator may comprise at least one thermocouple provided in or on the substrate. Similarly, in embodiments comprising the second sensor device, the second integrated circuit may comprise a substrate and the second thermoelectric generator may comprise at least one thermocouple provided in or on the substrate. In some embodiments, a single substrate may be used for the substrate of the first integrated circuit and the second integrated circuit such that these are part of the same integrated circuit. Embodiments may comprise plural thermocouples in the form of a thermopile.

In embodiments, the first temperature sensor is located proximate to or in contact with the at least one thermocouple of the first thermoelectric generator. In certain embodiments where a second sensor device is present, additionally or alternatively, the second temperature sensor may be located proximate to or in contact with the at least one thermocouple of the second thermoelectric generator. That is, in embodiments, a temperature sensor of a sensor device may be integrated into an integrated circuit with the thermoelectric generator such that it is adjacent to or in contact with at least one thermocouple of the thermoelectric generator. Embodiments provide improved accuracy as a result of the close relationship between the temperature sensor and thermoelectric generator. Embodiments may also be more compact while improving this performance and can provide improved manufacturing processes as a result of the ability to use semiconductor fabrication processes. The temperature sensor may be located within the integrated circuit so that it is in series with the thermoelectric generator. That is, in embodiments, the heat flux sensor can be located between the temperature sensor and the surface or the temperature sensor can be located between the surface and the heat flux sensor.

In certain embodiments, the first temperature sensor or the second temperature sensor may be embedded or incorporated into the substrate layer of the first integrated circuit or second integrated circuit. For example, where a single integrated circuit is present these may be integrated into the single substrate.

In certain embodiments, the first integrated circuit may further comprise a capping layer provided over the at least one thermocouple opposite the substrate layer and the first temperature sensor may be embedded in one of the capping layer of the first integrated circuit. In certain embodiments where a second sensor device is present, additionally or alternatively, the second integrated circuit may further comprise a capping layer provided over the at least one thermocouple opposite the substrate layer and the second temperature sensor may be embedded in the capping layer of the second integrated circuit. As such, the integration of the sensor into the integrated circuit may be achieved by embedding or incorporating the temperature sensor in one of a capping layer or a substrate layer (device layer or die) of its respective thermoelectric generator. The substrate layer and/or capping layer may comprise silicon or be a silicon layer.

In certain embodiments, wherein the first temperature sensor is located on or adjacent to one of: a backside of the substrate, and a frontside of a capping layer provided over the at least one thermocouple. Backside and frontside are relative to the part of the device that is to be placed on the surface of an object. This can be located on or adjacent an inner face of the substrate of its respective integrated circuit or, where present, located on or adjacent an inner face of the capping layer of its respective integrated circuit. This may further improve accuracy.

The first thermoelectric generator and the second thermoelectric generator can have different thermal resistances (or thermal conductivities). In certain embodiments, the first thermoelectric generator may have a first thermocouple configuration and the second thermoelectric generator may have a second thermocouple configuration and the first and second thermocouple configurations may be different so as to provide (e.g. contribute to, or entirely provide) the different first and second thermal resistances of the first and second thermoelectric generators. In other words, the thermocouples of each thermoelectric generator may be configured such that the first and second thermoelectric generators have a different thermal resistance.

In embodiments, the thermocouple configuration refers to arrangement of the thermocouples. For example, this may be the number of thermocouples (for example, where the first and second thermoelectric generators contain otherwise identical thermocouples), the area that the thermocouples occupy in or on the substrate (also referred to as the "fill factor") (for example, where a cross section is taken parallel to substrate), the thermal resistance of the materials used in the thermocouples, the height of the thermocouples or any combination thereof. Embodiments where the thermoelectric generators are provided as integrated circuits make this customisation more straightforward as the configuration (e.g. fill factor, number, etc.) of the thermocouples within the thermoelectric generator (e.g. the die) can more easily be modified. The thermal resistance can also be more accurately scaled in this configuration. In embodiments where the fill factor is modified, this advantageously provides a difference in thermal resistance in the thermoelectric generators without reducing the overall thickness of the assembly and without otherwise requiring modifications to the other parts of the assembly, as in the cases of configurations where additional layers of insulating materials are added. In an embodiment, the first thermoelectric generator may comprise a first plurality of thermocouples and the second thermoelectric generator may comprise a second plurality of thermocouples and the number of thermocouples in the first and second thermoelectric generators may be different so as to provide (e.g. contribute to, or entirely provide) the different first and second thermal resistances of the first and second thermoelectric generators. In some embodiments, the thermocouples in each of the first and second thermoelectric generators may otherwise be substantially identical or identical such that variation of the thermopile configuration as set out above provides a difference in thermal resistance.

In certain embodiments, the first or second thermoelectric generators may comprise an insulating layer so as to provide (e.g. contribute to, or entirely provide) the different first and second thermal resistances of the first and second thermoelectric generators. The insulating layer is, in embodiments, a part of the integrated circuit. For example, in an embodiment, the insulating may be provided on an outside face of the thermoelectric generator, such as on the outside of the substrate layer or die of the thermoelectric layer. In embodiments, this can be used in addition to or alternatively to the different thermocouple configurations. This allows for modification of the thermal resistance during fabrication without the drawbacks typically associated with modification of thermal resistance. For example, due to the sensitivity provided by the use of the integrated circuits, the insulation layer need not be as thick as previously required and in turn this means that sensitivity is not further reduced by the insulation layer.

In an embodiment, a core temperature sensing assembly for determining a core temperature of an object when positioned on a surface of the object may comprises a first sensor device for placement at a first surface location and a second sensor device for placement at a second surface location. The first sensor device may comprises a first heat flux sensor configured to measure heat flux at the first surface location and a first temperature sensor configured to measure temperature at the first surface location. The second sensor device may comprise a second heat flux sensor configured to measure heat flux at the second surface location and a second temperature sensor configured to measure temperature at the second surface location. The first heat flux sensor may comprise a first thermoelectric generator and the second heat flux sensor may comprise a second thermoelectric generator. Further, the first thermoelectric generator may comprise at least one first thermocouple having a first thermocouple configuration and the second thermoelectric generator comprises at least one second thermocouple having a second thermocouple configuration, the first and second thermocouple configurations being different such that the thermal resistance of the first thermoelectric generator is different to the second thermoelectric generator.

In certain embodiments, the sensing assembly is configured to cause the first thermoelectric generator of the first sensor device to actively heat or cool the first surface location. In other words, the thermoelectric generator may also act as a heater or cooler (as a Peltier device). A thermoelectric generator can also be used to generate a temperature gradient through the generator by the application of electrical energy. Providing an electrical current causes one side of the device to become hot and the other cold, which can be used to heat or cool the object on which the assembly is placed. The use of the heat flux sensor as a heating or cooling element can provide additional functionality to the device while maintaining a compact size and efficiency. In contrast, existing devices rely on external heating or cooling devices. In further embodiments, the sensing assembly is further configured to cause the second thermoelectric generator to actively heat or cool the second surface location. In embodiments, the application of heating or cooling via a thermoelectric generator can be used to probe the thermal response of the surface or the core of the object, which could in a non-limiting example be used to gather potentially providing useful information about health and activity level of wearer where the object is a person or animal. For example, in embodiments, heat or cooling may be applied to change the temperature from a baseline surface or core temperature, the heat or cooling may be halted and the time to recover to the baseline temperature may be monitored. The active heating or cooling may also be used to calibrate the sensing assembly. For example, the sensing assembly may be adapted to determine the core temperature in a calibration function or $R_{object}$ by heating or cooling the surface until there is a net zero heat flux at the surface. At that point, $T_{surface}=T_{core}$.

In certain embodiments, the sensing assembly may comprise a controller adapted to cause the first and/or second thermoelectric generator to actively heat or cool the first surface location. In certain embodiments, the sensing assembly of the embodiments defined herein may be provided as part of a system and the system may further comprise a controller adapted to cause the first and/or second thermoelectric generator to actively heat or cool the first surface location. By actively it is meant that a current is applied to the thermoelectric generator(s) to generate a temperature gradient across the device such that the generator acts as a Peltier device. Signals from the sensors of the sensor devices may be processed by the controller to monitor parameters of the object on which the assembly is located.

In certain embodiments, the sensing assembly may further comprise an energy storage device and may be adapted to store electrical energy generated by the TEG(s) in the energy storage device. This may be used to power the sensing assembly and/or other components, for example when present in a larger system. That is, the temperature gradient generated across each TEG as a result of the temperature on the surface against which the TEG is provided generates a voltage and thus an electrical energy output (e.g. when the surface is hot). This electrical energy can be stored in a storage device, such as a battery, and advantageously used to power the assembly or another component.

In an embodiment, a core temperature sensing assembly for determining a core temperature of an object when positioned on a surface of the object may comprise a first sensor device for placement at a first surface location, the first sensor device comprising: a first heat flux sensor configured to measure heat flux at the first surface location and output a first heat flux signal; and a first temperature sensor configured to measure temperature at the first surface location and output a first temperature signal, wherein the first heat flux sensor may comprise a first thermoelectric generator configured to measure heat flux at the first surface location and wherein the sensing assembly may be further configured to cause the first thermoelectric generator of the first sensor device to actively heat or cool the first surface location.

In certain embodiments, a core temperature sensing system may comprise any of the core temperature sensing assembly embodiments disclosed herein, and may further comprise a controller (or a processing unit). The controller may be configured to receive the first heat flux signal from the first heat flux sensor; receive the first temperature signal from the first temperature sensor; and calculate a core temperature based on the measured heat flux from the first heat flux signal and the measured temperature from the first temperature signal. The calculations may be based on the single heat flux principle and may be according to equation 1, for example.

In certain embodiments, a core temperature sensing system may comprise any of the core temperature sensing assembly embodiments disclosed herein which comprise first and second sensor devices and may further comprise a controller. The controller may be configured to: receive the first heat flux signal from the first heat flux sensor; receive the first temperature signal from the first temperature sensor; receive the second heat flux signal from the second heat flux sensor; receive the second temperature signal from the second temperature sensor; and calculate a core temperature based on the measured heat flux from the first heat flux signal, the measured temperature from the first temperature signal, the measured heat flux from the second heat flux signal and the measured temperature from the second temperature signal. The calculations may be based on the dual heat flux principle and may be according to equation 6, for example. The calculation may further comprise calculating $R_{object}$ based on equation 7.

The signals may relate to measurements taken simultaneously or substantially simultaneously. The measurements may be continuously taken so that the core temperature can be measured continuously, or the measurements may be taken at discrete intervals.

In embodiments, the controller may be a part of the assembly (for example, the assembly comprises the controller) or it may be external to the assembly. For example, the controller may be provided in an external device. In an embodiment, the assembly may include a transmitter for transmitting signals to the controller.

The controller may be implemented in any suitable manner, with software and/or hardware, to perform the various functions required. The controller may, for example, employ one or more microprocessors programmed using software (for example, microcode) to perform the required functions.

Examples of processor components that may be employed in various embodiments of the present disclosure include, but are not limited to, conventional microprocessors, application specific integrated circuits (ASICs), and field-programmable gate arrays (FPGAs).

In various implementations, the controller may be associated with one or more non-transitory storage media such as volatile and non-volatile computer memory such as RAM, PROM, EPROM, and EEPROM.

The non-transitory storage media may be encoded with one or more programs that, when executed on one or more processors and/or controllers, perform the required functions. Various storage media may be fixed within a processor or may be transportable, such that the one or more programs stored thereon can be loaded into the signal processing.

In some non-limiting examples, the system includes a user interface, such as a display, for communicating the core temperature determined by the controller to a user. Alternatively or additionally, the system may include a communications interface device, such as a wireless transmitter, configured to transmit the core temperature and/or sensed data to an external device, such as a personal computer, tablet, smartphone, remote server, etc.

In certain embodiments, a method for determining a core temperature of an object may comprise receiving a first heat flux signal from a first heat flux sensor of a first sensor device relating to a measured first heat flux and receiving a first temperature signal from a first temperature sensor of the first sensor device relating to a measured first temperature, the first heat flux sensor being a first thermoelectric generator and the first sensor device comprising a first integrated circuit comprising the first thermoelectric generator; and calculating a core temperature based on the first heat flux signal and the first temperature signal (i.e. using the measured first heat flux and measured first temperature). In a non-limiting example, calculating may comprise calculating based on the single heat flux method disclosed herein.

In certain embodiments, a method for determining a core temperature of an object may comprise may comprise: receiving a first heat flux signal from a first heat flux sensor of a first sensor device relating to a measured first heat flux and receiving a first temperature signal from a first temperature sensor of the first sensor device relating to a measured first temperature, where the first heat flux sensor is a first thermoelectric generator and where the sensing assembly comprises a first integrated circuit comprising the first thermoelectric generator. The method also comprises receiving a second heat flux signal from a second heat flux sensor of a second sensor device relating to a second measured temperature and receiving a second temperature signal from a second temperature sensor of the second sensor device relating to a second measured heat flux, where the second heat flux sensor is a second thermoelectric generator and where the sensing assembly comprises a second integrated circuit comprising the first thermoelectric generator. The method further comprises calculating a core temperature based on the first heat flux signal, the first temperature signal, the second heat flux signal and the second temperature signal (i.e. using the measured first heat flux, first temperature, second heat flux and second temperature). In an embodiment, calculating may comprise calculating based on the dual heat flux method disclosed herein.

In certain embodiments, a computer program may comprise computer program code which is configured, when said computer program is run on one or more physical computing devices, to cause said one or more physical computing devices to implement any of the method disclosed herein In certain embodiments, one or more non-transitory computer readable media may have a computer program stored thereon, the computer program comprising computer program code which is configured, when said computer program is run on one or more physical computing devices, to cause said one or more physical computing devices to implement any of the method disclosed herein.

FIG. 1 provides a schematic cross-sectional view through a sensing assembly 100 located on the surface 10 of an object 1. The sensing assembly 100 comprises a first sensor device 110, the first sensor device 110 comprising a first temperature sensor 120, and a first integrated circuit 125. The first integrated circuit 125 comprises a first heat flux sensor in the form of a first thermoelectric generator (TEG) 130. The object 1 includes a surface 10 and a core 12.

In the non-limiting example depicted in FIG. 1, the first sensor device 110 of the sensing assembly 100 is located on the surface of the object at a first surface location. The first temperature sensor 120 is arranged in the sensing assembly 100 so as to contact the surface 10 of the object 1. In this configuration, the first temperature sensor 110 will measure a temperature at the first surface location and output a first temperature signal to a controller (not shown) relating to the temperature ($T_1$). The first integrated circuit 125, which integrated circuit 125 comprises first TEG 130, is also provided on the surface 10 of the object 1 at the same first location and is configured to measure heat flux at the first surface location and output a first heat flux signal to the controller relating to the heat flux (q1). The structure of first integrated circuit 125 and first TEG 130 is disclosed in more detail, below, with respect to FIG. 2

Figure 2:
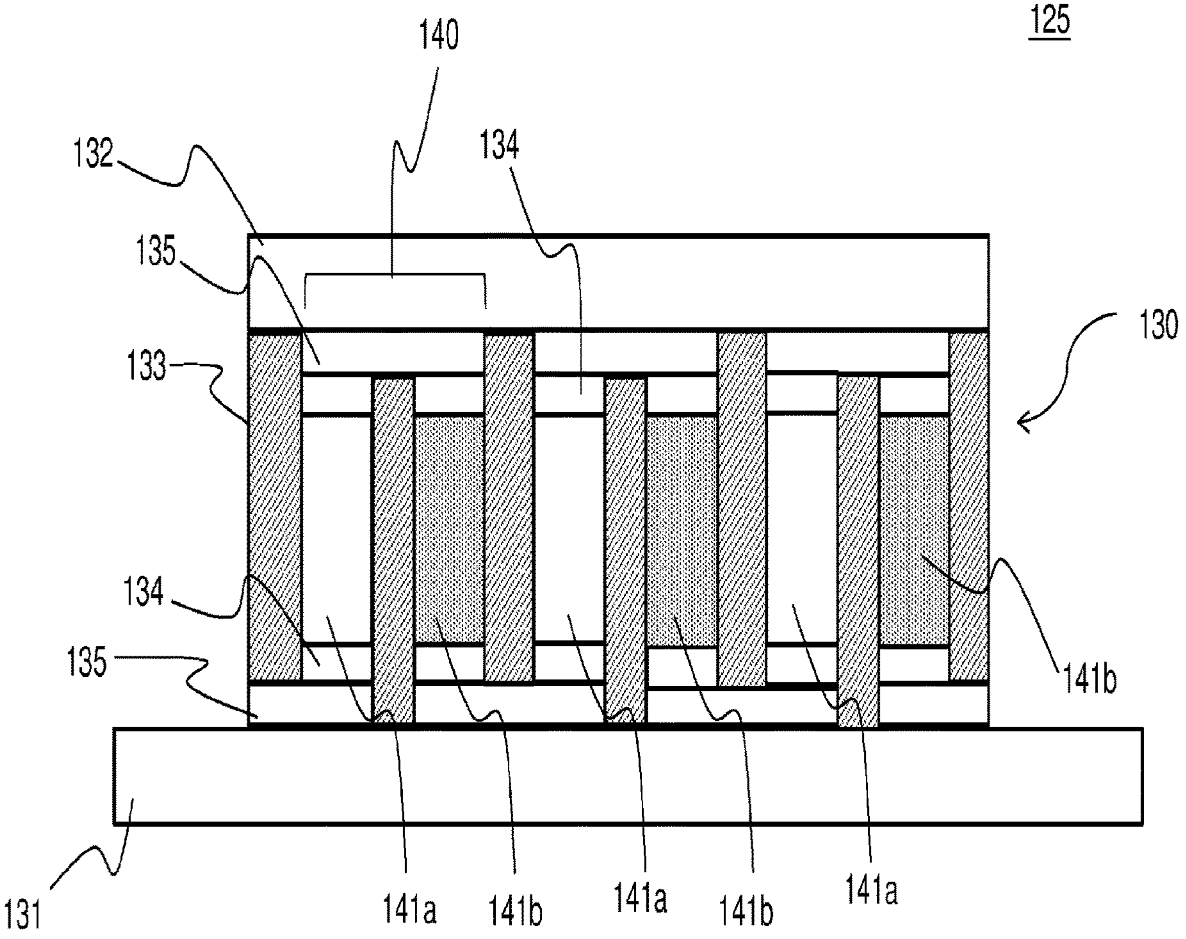
FIG. 2 provides a schematic cross-sectional view of an integrated circuit for use in an embodiment.

FIG. 2 depicts a non-limiting example of an integrated circuit 125 comprising a first TEG 130 according to an embodiment. In a non-limiting example, the integrated circuit 125 corresponds to the integrated circuit 125 depicted in FIG. 1. The integrated circuit 125 in this embodiment consists of a first TEG 130 and is formed as a single wafer. The first TEG 130 comprises a substrate layer 131 onto which a plurality of thermocouples 140 are formed. In a non-limiting example, each thermocouple 140 comprises two thermoelectric elements 141_a_, 141_b_. The thermoelectric elements 141_a_, 141_b_ may be formed of different types of thermoelectric materials such that each thermocouple 140 comprises a first thermoelectric material 141_a_ and a second thermoelectric material 141_b_. For example, the thermoelectric elements 141_a_ may be a p-type thermoelectric material and the thermoelectric elements 141_b_ may be an n-type thermoelectric material. Thermal contacts 134 are provided at the ends of each of the thermoelectric elements 141_a_, 141_b_ and connectors 135 are provided between the thermoelectric elements 141_a_, 141_b_ so that each thermocouple 140 is connected to an adjacent thermocouple 140 and the temperature gradient across all thermocouples 140 is measured. The thermocouples 140 are located within a dielectric layer 133 and a thermal contact layer 132 is provided above the dielectric layer 133 and thermocouples 140. The dielectric layer 133 has a high thermal resistance to avoid heat conduction through the dielectric layer 133. The thermal contact layer 132 can be an electrically insulating but thermally conductive layer. The structure of the first TEG 130 is vertical such that the thermal contact layer 132 defines the top of the first TEG 130 and the substrate 131 is provided at the bottom of the first TEG 130.

The structure of the first TEG 130, and in particular the thermocouples 140 and the materials used therein, is such that a difference in temperature between the top and bottom of the first TEG 130 results in a temperature gradient across the first TEG 130, and in particular across the height of the thermocouples 140. This temperature gradient and causes a flow of charge carriers within each of the thermoelectric elements 141_a_, 141_b_. In this embodiment, the material used in the first thermoelectric elements 141_a_ is selected so that the flow of charge carriers is in a first direction (for example, from the bottom of the first TEG 130 to the top) and the material used in the second thermoelectric elements 141_b_ is selected so that the flow of charge carriers is in an second, opposite direction (for example, from the top of the first TEG 130 to the bottom). For example, thermoelectric element 141$a$ may include p-type material such that positive charge carriers flow from a hot end to an opposite cold end and thermoelectric element 141$b$ may include n-type material such that electrons flow from an end having the heat source to the opposite end which is cooler. This generates a voltage output which directly relates to heat flux. This voltage can be used as a first heat flux signal, or may be used to generate the first heat flux signal. The heat flux through the object 1 and sensing assembly 100 is depicted in FIG. 1 as arrow q1. The material used for thermoelectric elements 141$a$, 141$b$ should have a high thermal resistance to maintain a temperature difference between the hot and cold sides of the thermoelectric elements 141$a$, 141$b$.

Referring back to FIG. 1, by placing the first TEG 130 on the surface 10 of the object 1, contact of one side of the first TEG 130 (e.g. the bottom end) will cause a temperature difference between the two opposing sides of the first TEG 130. For example, the substrate 131 side of the thermoelectric elements 141$a$, 141$b$ may be hotter due to contact with the surface 10 of the body 1 if the surface 10 has a temperature above the ambient temperature, and will therefore be designated as the "hot" side. The opposite side of the thermoelectric elements 141$a$, 141$b$ is therefore the "cold" side. The warmer body temperature generates the thermal gradient across the first TEG 130, resulting in a voltage output.

The measured heat flux from the first heat flux signal from the first TEG 130 and the measured temperature from the first temperature signal from the first temperature sensor 120 can then be used to calculate a core temperature. The non-limiting example of FIG. 1 has an assembly with a single sensor device 110 and therefore the single heat flux calculation method can be used to calculate the temperature of the core 12 of object 1. For example, equation 1, reproduced below, can be used to estimate the core temperature ($T_{core}$) based on the first temperature ($T_1$) signal, the first heat flux (q1) signal and an estimate of the thermal resistance of the object between the core and the surface ($R_{object}$):

$$T_{core} = T_1 + q_1 * R_{object} \quad \text{[equation 1]}$$

$R_{object}$ can be estimated to provide the $T_{core}$ value e.g. using any known method in the art.

The calculation can be carried out by the controller (not shown) or the signals may be transmitted to an external device for calculation.

The use of the integrated circuit 125 can be particularly advantageous due to the ability to structure a high density of thermocouples leading to improved sensitivity. Moreover, the integrated circuit 125 can be sufficiently compact such that size of the overall assembly is reduced despite the increased sensitivity, compared to prior art heat flux sensors.

The configuration of the thermocouples 140 in this embodiment can provide further performance advantages. For example, connecting the thermoelectric elements 141$a$, 141$b$ in an array (e.g. using connectors 135) may lead to improved sensitivity as the voltages across each of the thermoelectric elements 141, 141$b$ are combined and even small changes may be detectable.

Figures 3A, 3B:
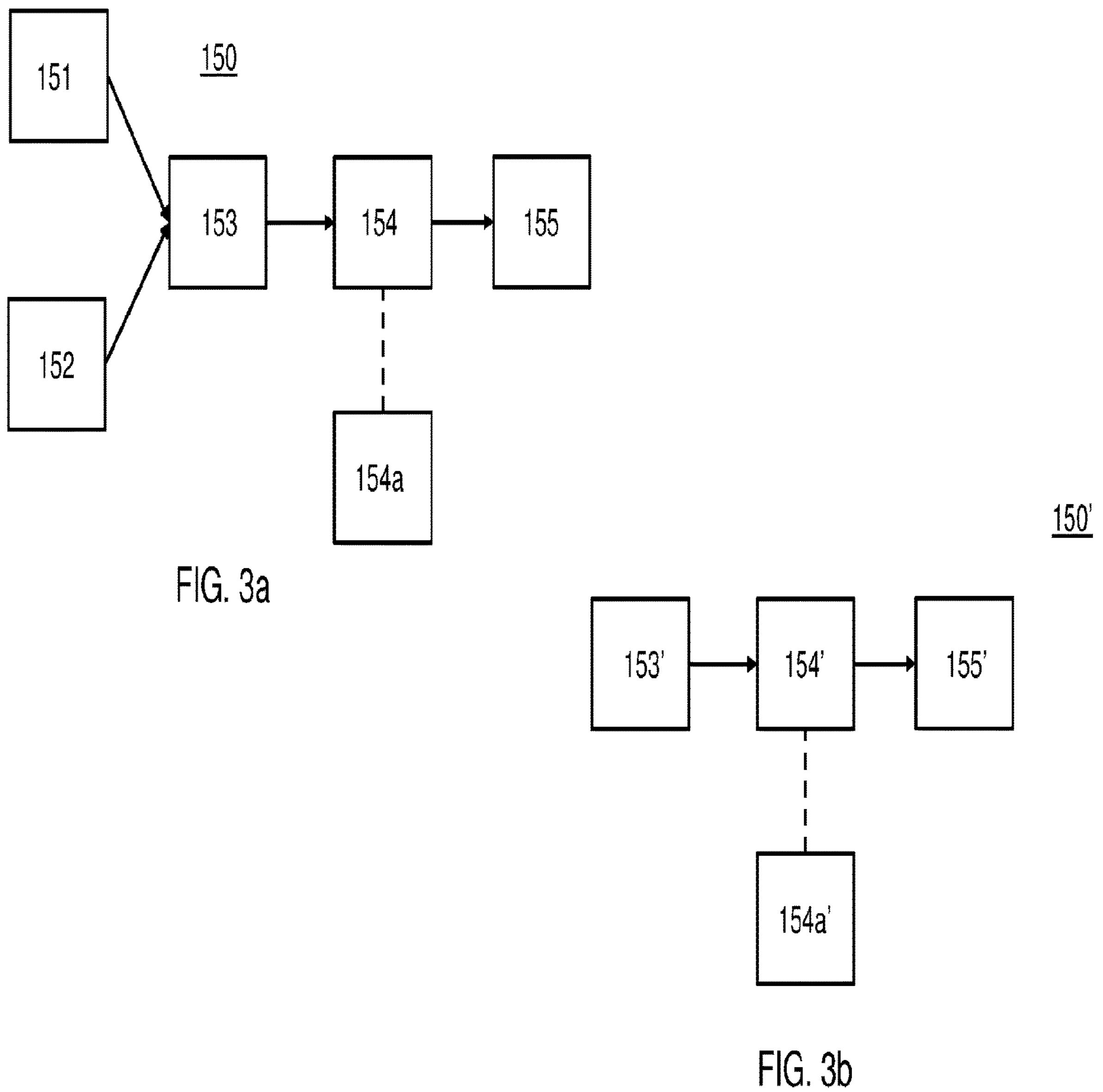
FIGS. 3*a* and 3*b* provide flow charts of a method according to an embodiment.

FIGS. 3$a$ and 3$b$ show flow charts depicting embodiments of methods of determining a core temperature of an object. In non-limiting examples, these could be used in conjunction with an assembly with a single sensor device such as the embodiment described in relation to FIGS. 1 and 2.

FIG. 3$a$ depicts a method 150 which could be carried out on or in conjunction with an assembly such as that depicted in FIGS. 1 and 2. The method 150 comprises measuring 151$a$ first temperature ($T_1$) using a first temperature sensor and outputting a first temperature signal based on $T_1$; measuring 152 a first heat flux ($q_1$) using a first heat flux sensor and outputting a first heat flux sensor signal based on $q_1$; receiving 153 (e.g. at a controller or processing unit) the first heat flux signal and the first temperature signal; and calculating 154 a core temperature ($T_{core}$) based on the first heat flux ($q_1$) (from the first heat flux signal) and the first temperature ($T_1$) (from the first temperature signal). The method may also comprise displaying 155 the calculated core temperature ($T_{core}$).

It will be appreciated that the steps of measuring 151 the first temperature ($T_1$) and measuring 152 the first heat flux ($q_1$) may be carried out simultaneously or substantially simultaneously. It will be appreciated that each corresponding signal contains or is directly related to the measured value.

FIG. 3 $b$ depicts a method 150' for determining a core temperature ($T_{core}$) of an object which could be carried out on a controller or signal processing unit provided as part of the assembly, such as that depicted in FIGS. 1 and 2, or external to an assembly. The method 150' comprises receiving 153' a first heat flux signal from a first heat flux sensor relating to a first measured heat flux (q1) and a first temperature signal from a first temperature sensor relating to a first measured temperature ($T_1$), and calculating 154' a core temperature based on the first heat flux ($q_1$) (from the first heat flux signal) and the first temperature ($T_1$) (from the first temperature signal). The method may also comprise displaying 155' the calculated core temperature ($T_{core}$).

The step of calculating 154, 154' a core temperature ($T_{core}$) in both of the methods 150, 150' based on the first heat flux signal and the first temperature signal may comprise estimating 154$a$, 154$a$' a value of $R_{object}$ if the method is a single heat flux method. This may be carried out as part of the calculation 154, 154' or may have been carried out prior to the measurement. For example, $R_{object}$ may be a constant or variable determined in advance.

Figure 4:
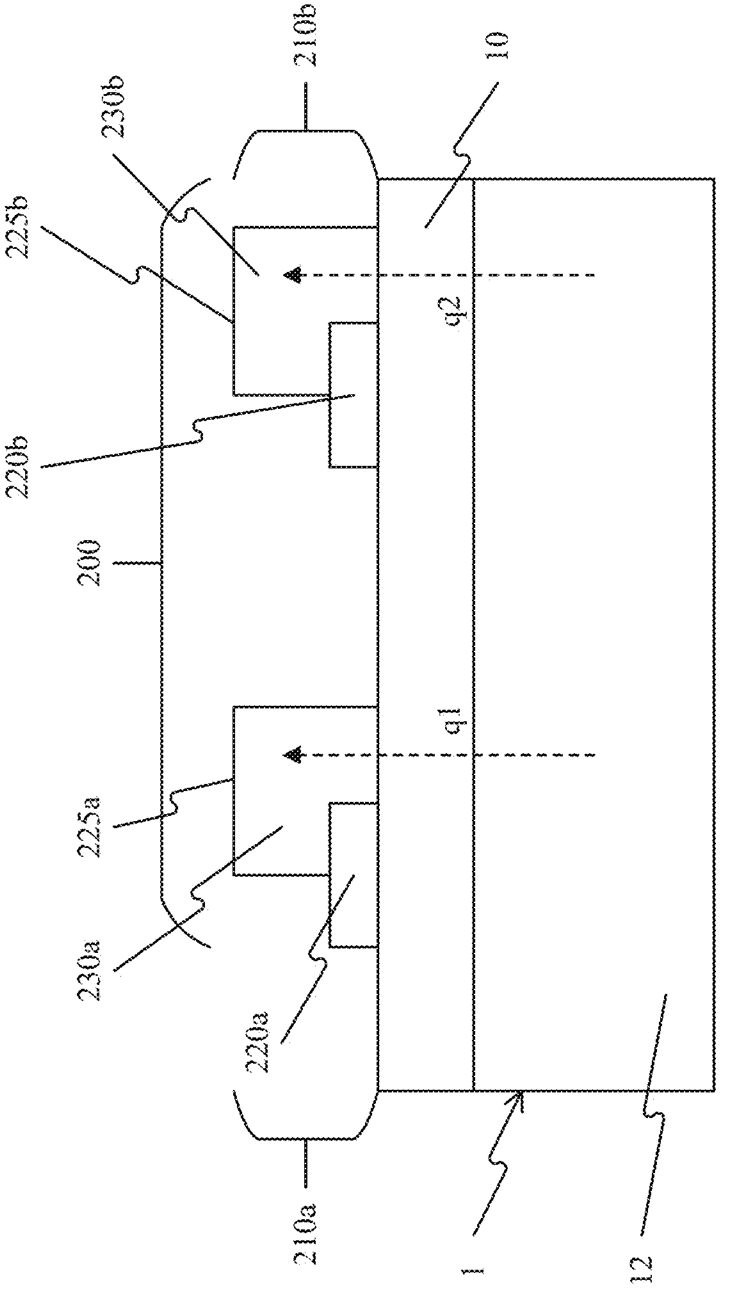
FIG. 4 provides a schematic cross-sectional view of a sensing assembly according to an embodiment.
Figure 4:

FIG. 4 depicts a schematic cross-sectional view through a sensing assembly 200 located on the surface 10 of an object 1. The sensing assembly 200 comprises a first sensor device 210$a$ and a second sensor device 210$b$, which in this embodiment have substantially the same structure as the sensor device 110 disclosed in relation to FIGS. 1 and 2. The first sensor device 210$a$ comprises a first temperature sensor 220$a$ and a first integrated circuit 225$a$, which first integrated circuit 225$a$ comprises a first heat flux sensor in the form of a first thermoelectric generator (TEG) 230$a$. The second sensor device 210$b$ comprises a second temperature sensor 220$b$ and a second integrated circuit 225$b$, which second integrated circuit 225$b$ comprises a second heat flux sensor in the form of a second thermoelectric generator (TEG) 230$b$. The object 1 includes a surface 10 and a core 12.

In the embodiment depicted in FIG. 4, the sensing assembly 200 is provided on the surface 10 of the object 1. The first sensor device 210$a$ of the sensing assembly is located at a first surface location and the second sensor device 210$b$ is located at a second surface location. These each comprise a separate integrated circuit 225$a$, 225$b$ and are provided on their own respective substrates and are separated by a thermal gap. These can, for example, be provided as separate sensor devices 210$a$, 210$b$, or could be attached to a single component (e.g. a printed circuit board).

The first sensor device 210*a* comprises the first temperature sensor 220*a*, which is arranged in the sensing assembly 200 so as to contact the surface 10 of the object 1 at a first surface location. In this configuration, the first temperature sensor 210*a* will measure a temperature at the first surface location and output a first temperature signal to a controller (not shown). The first sensor device 210*a* also comprises first integrated circuit 225*a*, which first integrated circuit 225*a* comprises first TEG 230*a*. The structure of first integrated circuit 225*a* and first TEG 230*a* is, in embodiments, the same as first integrated circuit 125 and first TEG 130 of FIGS. 1 and 2. In other embodiments, the first integrated circuit 225*a* and first TEG 230*a* may have a different structure. First TEG 230*a* is provided on the surface 10 of the object 1 at the same first location and is configured to measure heat flux at the first surface location and output a first heat flux signal to the controller.

In this non-limiting example, the second sensor device 220*b* has the same general structure as the first sensor device 220*a*, with the exception of thermal resistance of the second TEG 230*b*, as will be described in more detail below. The second sensor device 210*a* comprises the second temperature sensor 220*b*, which is arranged in the sensing assembly 200 so as to contact the surface 10 of the object 1 at a second surface location. In this configuration, the second temperature sensor 210*b* will measure a temperature at the second surface location and output a second temperature signal to a controller (not shown). The second sensor device 210*b* also comprises second integrated circuit 225*b*, which second integrated circuit 225*b* comprises second TEG 230*b*. The structure of second integrated circuit 225*b* and second TEG 230*b* is, in embodiments, the same as first integrated circuit 125 and first TEG 130 of FIGS. 1 and 2. In other embodiments, the second integrated circuit 225*b* and second TEG 230*b* may have a different structure. Second TEG 230*b* is provided on the surface 10 at the same second location and is configured to measure heat flux at second surface location and output a second heat flux signal to the controller.

Although the first TEG 230*a* and second TEG 230*b* have the substantially the same structure, the thermal resistance of the first and second TEGs 230*a*, 230*b* are different. That is, the first TEG 230*a* has a first thermal resistance and the second TEG 230*b* has a second thermal resistance and the first and second thermal resistances are different. This allows for the sensing assembly 200 to determine core temperature using the dual heat flux method.

The thermal resistance can be varied by a number of methods. As first and second TEGs 230*a*, 230*b* are advantageously provided in first and second integrated circuits 225*a*, 225*b*, the thermal resistance can be easily modified during fabrication without the drawbacks typically associated with modification of thermal resistance. In this non-limiting embodiment, although not depicted, the number of thermocouples in the second TEG 230*b* is reduced so as to change the fill factor of the thermocouples in the second integrated circuit 225*b*. This alters the thermal resistance of TEG 230*b*.

The heat flux through the object 1 and first sensor device 210*a* at the first surface location is depicted in FIG. 4 as arrow q1 and the heat flux through the object 1 and the second sensor device 210*b* at the second surface location is depicted as arrow q2. Both of first heat flux q1 and first heat flux q2 can be measured by the sensing assembly 210, specifically the first and second TEGs 230*a*, 230*b*, and signals corresponding to each will be output by their respective sensors. The first and second temperature sensors 220*a*, 220*b* can also measure the first and second temperatures, respectively, and output corresponding signals.

The core temperature of the object 1 can then be calculated from the sensor data, specifically first heat flux measurement (q1) from the first TEG 230*a*, first temperature ($T_1$) from the first temperature sensor 220*a*, second heat flux measurement (q2) from the second TEG 230*b* and second temperature ($T_2$) from the second temperature sensor 220*b*. The presence of first and second (i.e. two) sensor devices 210*a*, 220*b*, each of which is configured to determine heat flux and temperature, enables the use of the dual heat flux calculation method. For example, equation 6, reproduced below, can be used:

$$T_{core} = \frac{T_1 q_2 - T_2 q_1}{q_2 - q_1} \qquad \text{[equation 6]}$$

The thermal resistance of the object between the core and the surface ($R_{object}$) can also be calculated using equation 7:

$$R_{object} = \frac{T_{core} - T_1}{q_1} \text{ or } R_{object} = \frac{T_{core} - T_2}{q_2} \qquad \text{[equation 7]}$$

Figures 5A, 5B:
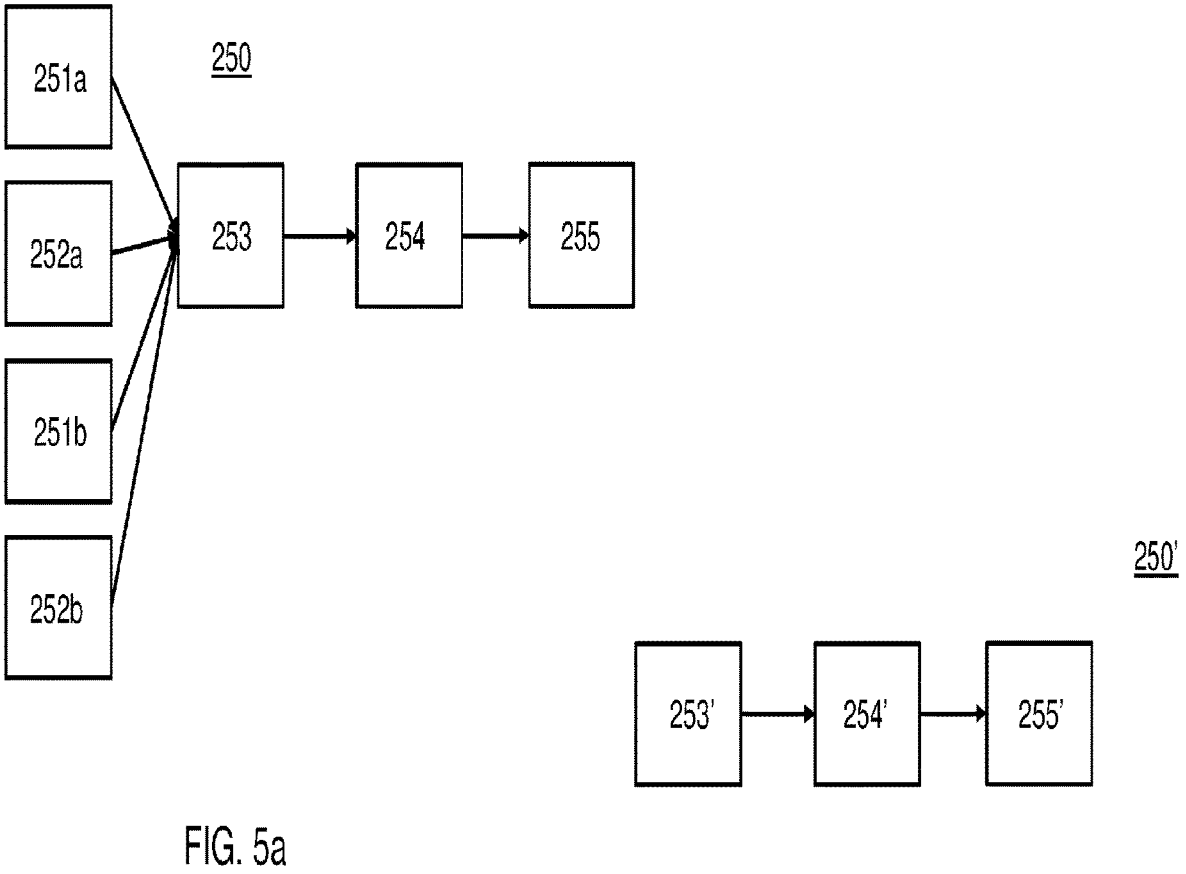
FIGS. 5*a* and 5*b* provide flow charts of a method according to an embodiment.

FIGS. 5*a* and 5*b* show flow charts depicting embodiments of methods of determining a core temperature of an object. In non-limiting examples, these could be carried out or used in conjunction with an assembly with two sensor devices such as the embodiment described in relation to FIG. 4.

FIG. 5*a* depicts a method 250 which could be carried out on or with an assembly such as that depicted in FIG. 4. The method 250 comprises measuring 251*a* a first temperature ($T_1$) using a first temperature sensor and outputting a first temperature signal from the first temperature sensor based on $T_1$; measuring 252*a* a first heat flux ($q_1$) using a first heat flux sensor and outputting a first heat flux sensor signal based on $q_1$; measuring 251*b* a second temperature ($T_2$) using a second temperature sensor and outputting a second temperature signal based on $T_2$; measuring 252*b* a second heat flux ($q_1$) using a second heat flux sensor and outputting a second heat flux sensor signal based on $q_2$; receiving 253 (e.g. at a controller or processing unit) the first heat flux signal, the first temperature signal, the second heat flux signal and the second temperature signal; and calculating 154 a core temperature ($T_{core}$) based on a first heat flux ($q_1$) (from the first heat flux signal), the first temperature ($T_1$) (from the first temperature signal), the second heat flux ($q_2$) (from the second heat flux signal) and the second temperature $T_2$ (from the second temperature signal). The method may also comprise displaying 255 the calculated core temperature ($T_{core}$).

It will be appreciated that the steps of measuring 251*a* the first temperature ($T_1$), measuring 252*a* the first heat flux ($q_1$), measuring 251*b* the second temperature ($T_2$) and measuring 252*b* the second heat flux may be carried out simultaneously or substantially simultaneously. It will be appreciated that each corresponding signal contains or directly relates to the corresponding measured value.

FIG. 5*b* depicts a method 250' for determining a core temperature ($T_{core}$) of an object which could be carried out on a controller or signal processing unit provided as part of the assembly or external to an assembly. The method 250 comprises receiving 253' a first heat flux signal from a first heat flux sensor relating to a first measured heat flux (q1). a first temperature signal from a first temperature sensor relating to a first measured temperature ($T_1$), a second heat flux signal from a second heat flux sensor relating to a second measured heat flux ($q_2$) and a second temperature signal from a second temperature sensor relating to a second measured temperature ($T_2$). The method further comprises calculating 254' a core temperature ($T_{core}$) based on a first heat flux ($q_1$) (from the first heat flux signal), the first temperature ($T_1$) (from the first temperature signal), the second heat flux ($q_2$) (from the second heat flux signal) and the second temperature $T_2$ (from the second temperature signal). The method may also comprise displaying 255' the calculated core temperature ($T_{core}$).

Figure 6:
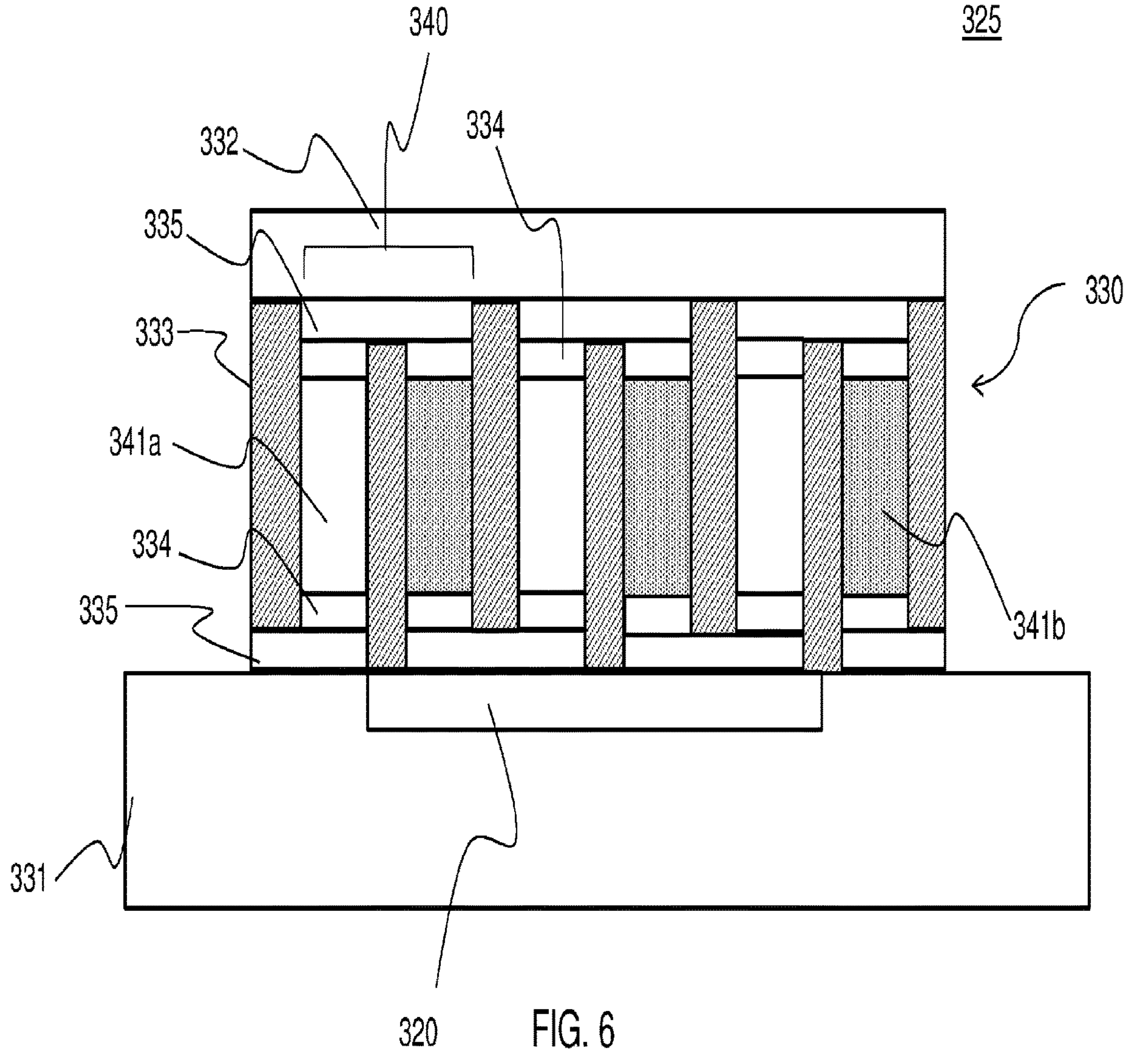
FIG. 6 provides a schematic cross-sectional view of an integrated circuit for use in an embodiment.

FIG. 6 depicts a depicts a non-limiting example of an integrated circuit 325 comprising a TEG 330 and a temperature sensor 320 that may be used in embodiments as a sensor device. For example, in embodiments, integrated circuit 325 could be used in place of the first sensor device 110 of FIGS. 1 and 2 or first or second sensor devices 210*a*, 210*b* of FIG. 4.

The integrated circuit 325 in this embodiment comprises both a TEG 330 and a temperature sensor 320 and is formed as a single wafer. By providing both the temperature sensor 320 and TEG 330 on the same chip, embodiments may provide improved accuracy and a smaller overall footprint of the device compared to existing sensor devices.

The TEG 330 part of integrated circuit 325 has the same structure as integrated circuit 125 of FIG. 2 and comprises a substrate layer (or die) 331, a plurality of thermocouples 340 comprised of thermoelectric elements 341*a*, 341*a* formed on the substrate layer 331, thermal contacts 334 provided at the ends of each of the thermoelectric elements 341*a*, 341*b* and connectors 335 provided between the thermoelectric elements 341*a*, 341 *b* so that each thermocouple 340 is connected to an adjacent thermocouple 340. The thermocouples 340 are located within a dielectric layer 333 and a thermal contact layer 332 is provided above the dielectric layer 333 and thermocouples 340.

As noted above, the integrated circuit 325 additionally comprises the temperature sensor 320. In this embodiment, the temperature sensor 320 is integrated into the substrate 331 and is in contact with the thermocouples 340. Without wishing to be bound by theory, by having the temperature sensor 320 in close proximity to the thermocouple, it is thought that this can reduce heat losses between the point at which heat flux is measured and point at which temperature is measured, and that by taking the measurements from the same precise area accuracy is increased.

FIGS. 7*a*-7*d* schematically depict alternative arrangements of integrating temperature sensors 420*a-d* into integrated circuits 425*a-d*. In these embodiments, integrated circuits 425*a-d* each comprise a substrate layer (or die) 431*a-d*, a capping layer (or cap) 436 provided over the substrate layer 431*a-d* and arranged to cover thermocouples (not shown) provided in or on the substrate layer 431*a-d*, and a temperature sensor 420*a-d*.

Figure 7A:
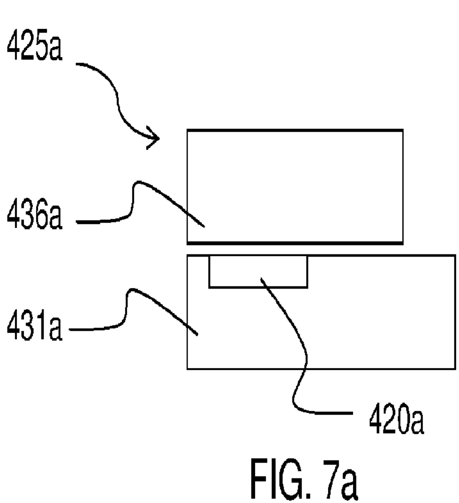
FIGS. 7*a-d* provide schematic views of integrated circuits for use in embodiments.
Figure 7B:
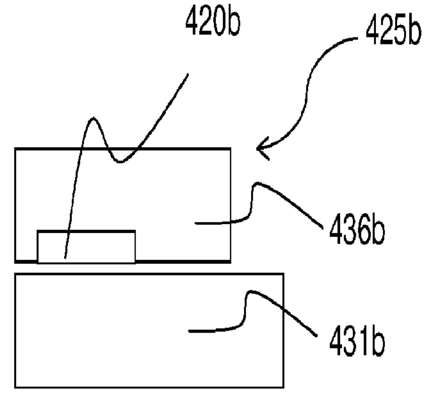

Each of FIGS. 7*a-d* shows a different arrangement of the respective temperature sensor 420*a-d* within the integrated circuits 425*a-d*. FIG. 7*a* shows an arrangement in which the temperature sensor 420*a* is provided on or in an inner (surface of the substrate layer 431*a*. In other words, it is located on or in the backside or rearside of the substrate layer 431*a* relative to the surface on which a device incorporating the integrated sensor 425*a* will be placed. FIG. 7*b* shows an arrangement in which the temperature sensor 431*b* is located on or in an inner surface of the capping layer 436*b*. In other words, it is located on or in the frontside of capping layer 436*b* relative to the surface on which a device incorporating the integrated sensor 425*b* will be placed. Without wishing to be bound by theory, embodiments in which a temperature sensor is integrated within the integrated circuit and located within the integrated circuit on or adjacent an inner surface can provide improved accuracy due to the proximity to the thermoelectric generator. In embodiments where a temperature sensor is located in front of or behind (e.g. in series with) the thermoelectric generator, accuracy can be further improved.

Figure 7C:
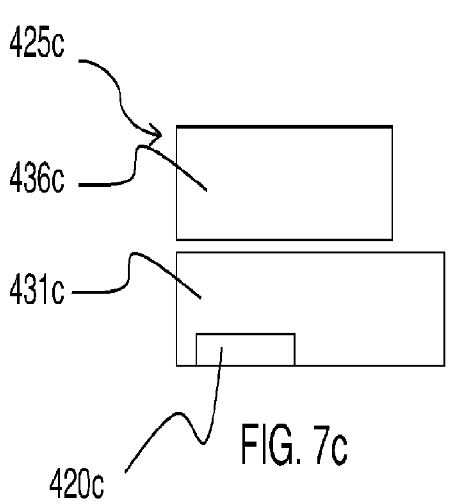
Figure 7D:
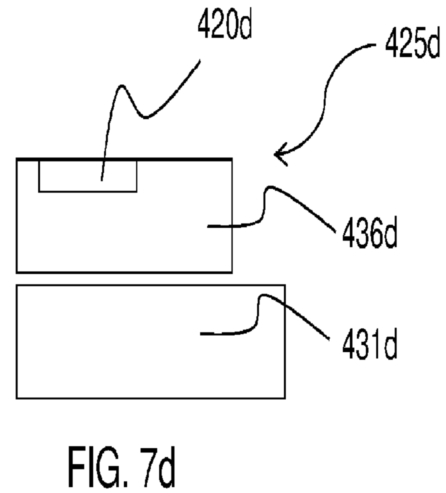

FIG. 7*c* shows an arrangement in which the temperature sensor 420*c* is provided on an outer surface of the substrate layer 431*c*. In other words, it is located on the frontside of the substrate layer 431*c* relative to the surface on which a device incorporating the integrated sensor 425*c* will be placed. FIG. 7*d* shows an arrangement in which the temperature sensor 431*d* is located on an outer surface of the capping layer 436*d*. In other words, it is located on the backside of capping layer 436*d* relative to the surface on which a device incorporating the integrated sensor 425*d* will be placed.

In non-limiting examples, all of the configurations depicted in FIGS. 7*a-d* can be achieved by providing the temperature sensor 420*a-d* within a recess on the respective surface of the substrate layer 431*a-d* or capping layer 436*a-d* or, alternatively, by providing the temperature sensor 420*a-d* directly in or on the substrate layer 431*a-d* or capping layer 436*a-d*. It may also be that temperature sensor 420*a-d* is formed in the substrate layer 431*a-d* or capping layer 426*a-d*. All of these configurations can be advantageously manufactured using semiconductor processing methods.

Figure 9:
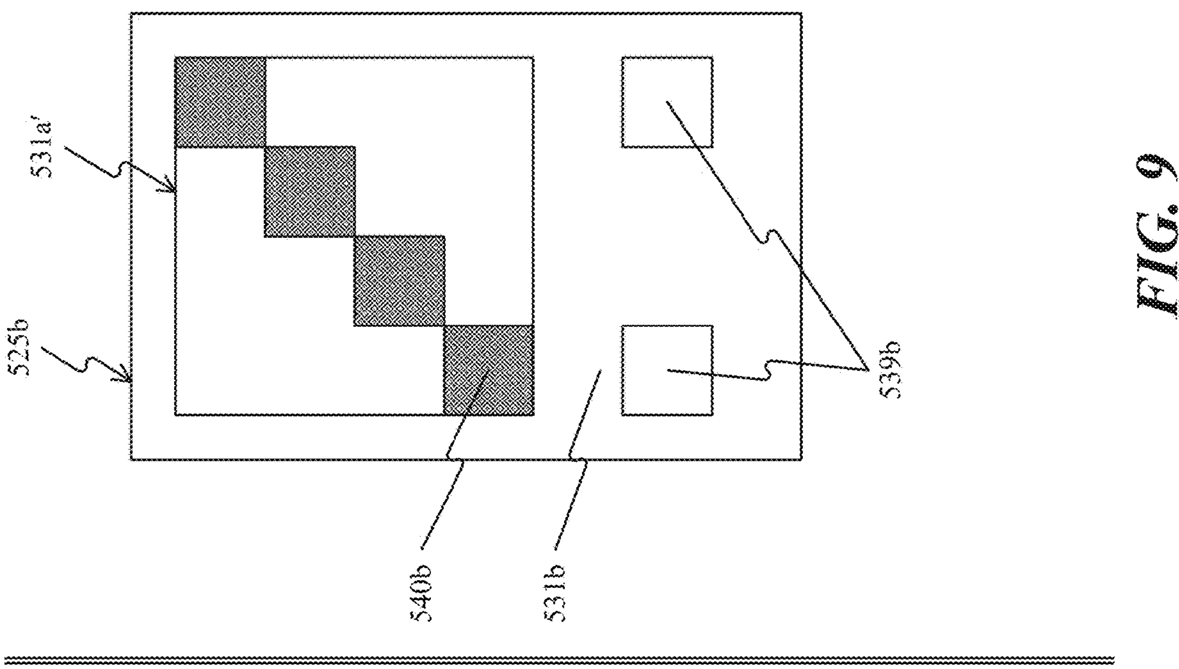
FIG. 9 provides a schematic cross-sectional plan view of an integrated circuit for use in an embodiment.
Figure 8:
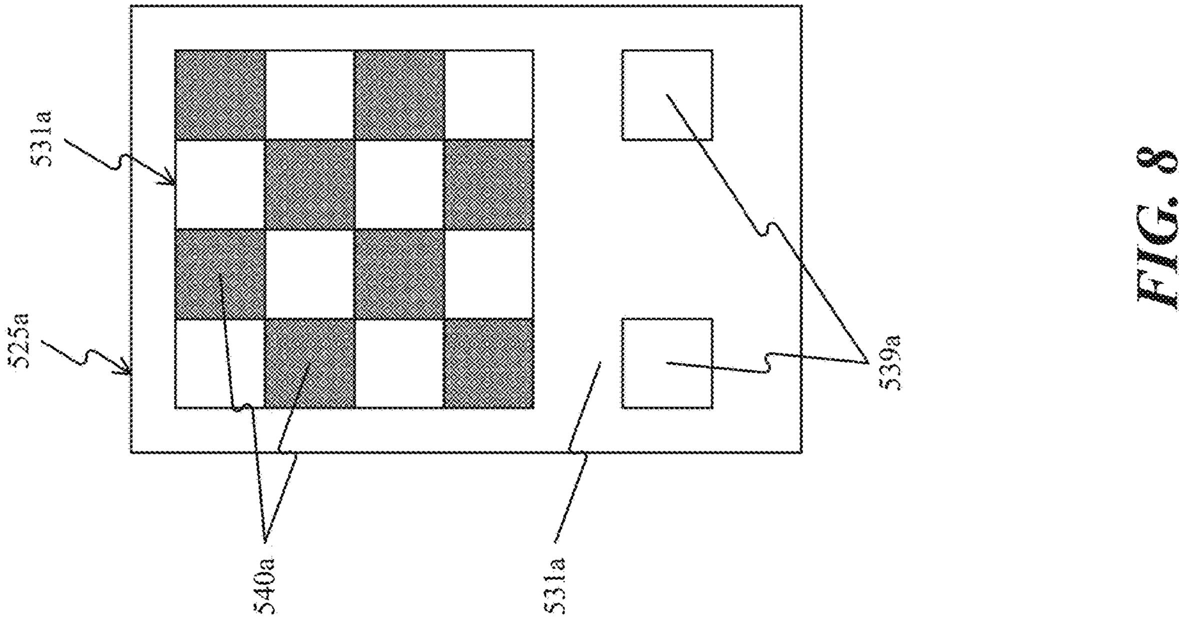
FIG. 8 provides a schematic cross-sectional plan view of an integrated circuit for use in an embodiment.

FIG. 8 depicts a plan cross-section of a first integrated circuit 525*a* and FIG. 9 depicts a plan cross-section of a second integrated circuit 525*b*. The first integrated circuit 525*a* shown in FIG. 8 comprises a substrate 531*a* with a substrate thermocouple portion 531*a*', electrical connectors 539*a* for connecting the first integrated circuit 525*a* to an external circuit and an array of thermocouples 540*a*. The second integrated circuit 525*b* shown in FIG. 9 comprises a substrate 531*b* with a substrate thermocouple portion 531*b*', electrical connectors or terminals 539*b* for connecting the first integrated circuit 525*b* to an external circuit and an array of thermocouples 540*b*.

FIGS. 8 and 9 together depict a means for providing two TEGs 525*a*, 525*b* with different thermal resistances such that an assembly comprising the two TEGs 525*a*, 525*b* can be used to calculate core temperature using the dual heat flux method.

In particular, the first TEG 525 *a* has a first thermopile configuration defined by the amount of the substrate thermocouple portion 531 *a*' which is covered by the thermocouples 540 *a*, which can be referred to as the "fill factor". In other words, the surface area occupied by the thermocouples when taking a section through the first TEG in a plane parallel to the substrate and viewing from a plan view. In the embodiment schematically depicted in FIG. 8, there is a 50% thermocouple coverage or fill factor. This gives the first TEG 525 *a* a first thermocouple configuration and a first thermal resistance. In the second TEG 525 *b* schematically depicted in FIG. 9, there is a 25% coverage (or fill factor) of thermocouples in the thermocouple substrate region 531 *b*'. This gives the second TEG 525 *b* a second thermocouple configuration, which is different to the first TEG 525 *a*, and a second thermal resistance, which is different to the first TEG 525 *a*. In a non-limiting example, assuming that the remainder of the construction of the integrated circuits 525

*a* and 525 *b* are the same, this can provide the first TEG 525 *a* with a thermal resistance that is double that of the second TEG 525 *b*.

The use of an integrated circuit enables the straightforward modification of the first and second TEGs 525*a*, 525*b* such that the different thermal resistances can be provided with minimal modification to the manufacturing process or the end device. For example, the use of an integrated circuit and this particular way of modifying the thermocouple configuration enables the first and second TEGs 525*a*, 525*b* to both remain compact and avoid increasing the height or bulk of the overall assemblies, which is often required when insulating layers are incorporated into bulk devices in the art. This can also avoid the drawbacks associated with separating the introducing insulating layers between a part of the TEGS 525*a*, 525*b* (i.e. the thermocouples) and the surface of the object on which the assembly will be placed.

FIG. 10 depicts a schematic drawing of an integrated circuit 625 in which the thermal resistance has been modified. Integrated circuit 625 includes a substrate layer 631 onto which a thermocouples are formed (not shown, a capping layer (or cap) 636 provided over the substrate layer 631 and arranged to cover the thermocouples (not shown) provided in or on the substrate layer 631, and an insulating layer 637. In this non-limiting example, insulating layer 637 is provided on the frontside of substrate layer 631. Insulating layer 637 adds additional thermal resistance to the integrated surface. By having the insulating layer 637 integrated into the integrated circuit 625 this can be advantageously manufactured using semiconductor processing methods. Moreover, due to the improved accuracy and sensitivity of embodiments using integrated circuit TEGS, insulating layers may be thinner and made from less thermally resistant materials than was previously the case, thus reducing any subsequent impact on accuracy and sensitivity.

It will be appreciated that although the thermal resistance modifications based on thermocouple configurations (e.g. shown in FIGS. 8 and 9) and insulating layers (e.g. shown in FIG. 10) have been depicted separately, in some embodiments these may be combined such that each modification contributes to a difference in thermal resistance.

FIG. 11 depicts a modified version of the sensing assembly 100 of FIG. 1. The sensing assembly 100' has the same structure as the sensing assembly 100 of FIG. 1, but has been modified so that the first TEG 130' of the sensing assembly 100' may also operate as a Peltier device. In particular, a circuit 126' has been added with a power source so that a current can be applied to first TEG 130'. In this way, depending on the direction of the current, the first TEG 130' can be used to heat or cool at least the surface 10 of the object 1 on which the sensing assembly 100' is located.

For example, in a non-limiting embodiment, a controller (not shown) could cause the first TEG 130' to heat the surface 10 (heat shown radiating out as pulses 15). The sensing assembly 100' assembly could then be used to monitor the response of the object 1 to the heat. For example, this could be used to monitor the time to recover to the original temperature, which can provide information on the object. The temperature sensor 120' could be used to track the response of the surface 10. FIG. 12 depicts a graph showing the temperature of the surface 12 ($T_{surface}$ on y axis) over time (x-axis) as monitored by the temperature sensor 120'. Peak A illustrates where the first TEG 130' is used to heat the surface and slope B shows the recovery to the baseline temperature after the heating has ceased.

In embodiments, use of first TEG 130' to heat the surface may be advantageous when monitoring core body temperature as the response of the patient can be monitored.

Figure 13:
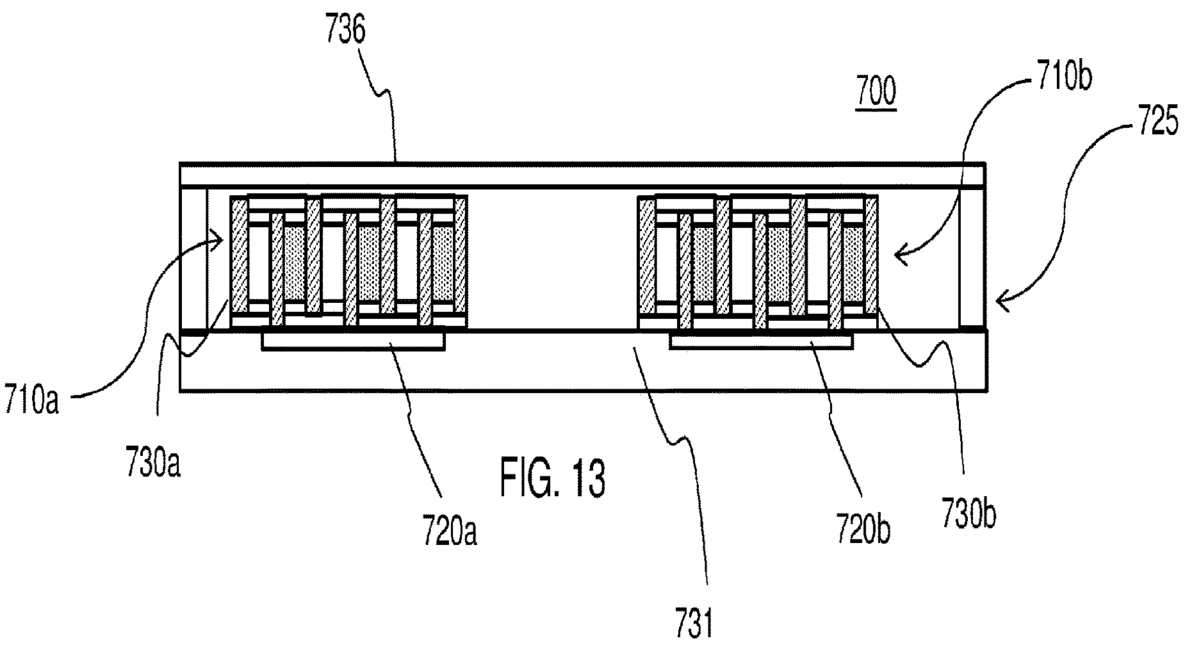
FIG. 13 provides a schematic cross-sectional view of a sensing assembly according to an embodiment.

FIG. 13 depicts an embodiment of a sensing assembly 700 comprising first and second sensor devices 710 *a*, 710 *b* which are both provided as part of a single integrated circuit 725. The integrated circuit 725 comprises a substrate 731 on which is provided a first thermoelectric generator 710 *a* and a first temperature sensor 720 *a*, together forming the first sensor device 710 *a*, and a second thermoelectric generator 710 *b* and a second temperature sensor 720 *b*, together forming the second sensor device 710 *b*. These sensor devices 710 *a*, 710 *b* are separated on the substrate 731 by a thermal gap and function as set out in respect of the abovementioned embodiments. A capping layer 736 is provided over the substrate 731. A first TEG 730 *a* and a second TEG 730 *b* are provided as part of integrated circuit 725.

Figure 14:
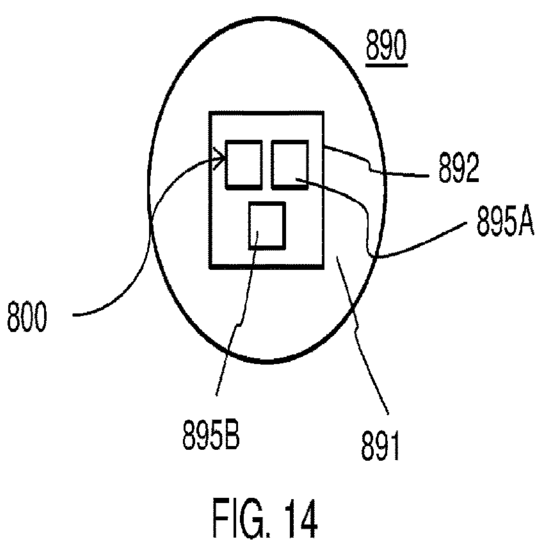
FIG. 14 provides a schematic perspective view of a sensing assembly according to an embodiment.

FIG. 14 depicts an implementation of an embodiment in the form of a chest patch 890 for monitoring core body temperature of a person comprising a sensing assembly 800. The sensing assembly 800 can be according to any embodiment disclosed herein.

The chest patch 890 can be used to determine the core body temperature of a patient (not shown) in a clinical or surgical setting. The patch 890 comprise an adhesive plaster 891 for adhering the patch 890 to the patient and a housing 892 comprising electronic components, including the sensing assembly 800. In some embodiments, the patch 890 may include additional sensors 895A, 895B in the housing 892 for detecting other parameters of interest, such as heart rate, EKG, $SpO_2$.

It should be understood that the detailed description and specific examples, while indicating exemplary embodiments of the apparatus, systems and methods, are intended for purposes of illustration only and are not intended to limit the scope. These and other features, aspects, and advantages of the apparatus, systems and methods of the present invention can be better understood from the description, appended claims or aspects, and accompanying drawings. It should be understood that the Figures are merely schematic and are not drawn to scale. It should also be understood that the same reference numerals are used throughout the figures to indicate the same or similar parts.

Other variations to the disclosed embodiments can be understood and effected by those skilled in the art in practicing the disclosure, from a study of the drawings, the disclosure, and the appended aspects or claims. In the aspects or claims, the word "comprising" does not exclude other elements or steps, and the indefinite article "a" or "an" does not exclude a plurality. The mere fact that certain measures are recited in mutually different dependent aspects or claims does not indicate that a combination of these measures cannot be used to advantage. Any reference signs in the claims should not be construed as limiting the scope.

The invention claimed is:

1. A core temperature sensing assembly to determine a core temperature of an object when positioned on a surface of the object, comprising:

- a first sensor device for placement at a first surface location, the first sensor device comprising:
  - a first heat flux sensor configured to measure a heat flux at the first surface location and output a first heat flux signal relating to the measured heat flux; and
  - a first temperature sensor configured to measure a temperature at the first surface location and output a first temperature signal relating to the measured temperature, wherein the first heat flux sensor is a first thermoelectric generator (TEG); and wherein the core temperature sensing assembly comprises a first integrated circuit comprising the first TEG.

2. The core temperature sensing assembly of claim 1, wherein the core temperature sensing assembly is further configured to cause the first TEG of the first sensor device to actively heat or cool the first surface location.

3. The core temperature sensing assembly of claim 1, further comprising a second TEG comprised in a second integrated circuit and configured to measure a heat flux at a second surface location and output a second heat flux signal relating to the measured heat flux, wherein the first integrated circuit and second integrated circuit are parts of a single unitary integrated circuit with a single substrate.

4. The core temperature sensing assembly of claim 1, wherein the first integrated circuit is a monolithic integrated circuit die.

5. The core temperature sensing assembly of claim 4, wherein the monolithic integrated circuit die comprises a substrate and a dielectric layer over the substrate, and wherein a plurality of thermoelectric elements of the first thermoelectric generator are disposed within the dielectric layer.

6. The core temperature sensing assembly of claim 1, wherein the first integrated circuit further comprises the first temperature sensor.

7. The core temperature sensing assembly of claim 6, wherein the first integrated circuit comprises a substrate and the first TEG comprises at least one thermocouple provided in or on the substrate; and wherein the first temperature sensor is located proximate to or in contact with the at least one thermocouple of the first TEG.

8. The core temperature sensing assembly of claim 7, wherein the first temperature sensor is located on or adjacent to one of: a backside of the substrate, and a frontside of a capping layer provided over the at least one thermocouple.

9. The core temperature sensing assembly of claim 1, further comprising a second sensor device for placement at a second surface location, the second sensor device comprising:

a second heat flux sensor configured to measure a heat flux at the second surface location and output a second heat flux signal relating to the measured heat flux; and a second temperature sensor configured to measure a temperature at the second surface location and output a second temperature signal relating to the measured temperature, wherein the second heat flux sensor is a second thermoelectric generator (TEG).

10. The core temperature sensing assembly of claim 9, wherein the first TEG has a first thermal resistance and the second TEG has a second thermal resistance; and wherein the first thermal resistance and the second thermal resistances are different.

11. The core temperature sensing assembly of claim 10, wherein the first TEG has a first thermocouple configuration and the second TEG has a second thermocouple configuration, wherein the first thermocouple configuration and the second thermocouple configuration are different so as to provide the different first thermal resistance and second thermal resistance, wherein the first thermocouple configuration and the second thermocouple configuration are each determined by a number of thermocouples, an area of a substrate covered by the thermocouples, a thermal resistance of materials used in the thermocouples, a height of the thermocouples, or any combination thereof.

12. The core temperature sensing assembly of claim 10, wherein one of the first TEG or the second TEG further comprises an insulating layer so as to modify a corresponding one of the first thermal resistance or the second thermal resistance.

13. The core temperature sensing assembly of claim 9 further comprising a second integrated circuit comprising the second TEG.

14. The core temperature sensing assembly of claim 13, wherein the first integrated circuit and the second integrated circuit are a single integrated circuit.

15. The core temperature sensing assembly of claim 13, wherein the second integrated circuit further comprises the second temperature sensor.

16. The core temperature sensing assembly of claim 15, wherein the second integrated circuit comprises a substrate and the second TEG comprises at least one thermocouple provided in or on the substrate; and wherein the second temperature sensor is located proximate to or in contact with the at least one thermocouple of the second TEG, wherein the first second temperature sensor is located on or adjacent to one of: a backside of the substrate, and a frontside of a capping layer provided over the at least one thermocouple.

17. A core temperature sensing system, comprising a core temperature sensing assembly comprising:

a first sensor device for placement at a first surface location, the first sensor device comprising:

a first heat flux sensor configured to measure a heat flux at the first surface location and output a first heat flux signal relating to the measured heat flux; and a first temperature sensor configured to measure a temperature at the first surface location and output a first temperature signal relating to the measured temperature, wherein the first heat flux sensor is a first thermoelectric generator (TEG); and wherein the sensing assembly comprises a first integrated circuit comprising the first TEG; and a controller configured to:

receive the first heat flux signal from the first heat flux sensor;

receive the first temperature signal from the first temperature sensor; and calculate a core temperature based on the measured heat flux from the first heat flux signal and the measured temperature from the first temperature signal.

18. The core temperature sensing system of claim 17, wherein the core temperature sensing assembly further comprises a second sensor device for placement at a second surface location, the second sensor device comprising:

a second heat flux sensor configured to measure a heat flux at the second surface location and output a second heat flux signal relating to the measured heat flux; and a second temperature sensor configured to measure a temperature at the second surface location and output a second temperature signal relating to the measured temperature, wherein the second heat flux sensor is a second thermoelectric generator; and wherein the controller is further configured to:

receive the second heat flux signal from the second heat flux sensor;

receive the second temperature signal from the second temperature sensor; and calculate the core temperature based on the measured heat flux from the first heat flux signal, the measured temperature from the first temperature signal, the measured heat flux from the second heat flux signal and the measured temperature from the second temperature signal.

19. The core temperature sensing system of claim 17, wherein the first integrated circuit further comprises the first temperature sensor.

20. The core temperature sensing system of claim 19, wherein the first integrated circuit comprises a substrate and the first TEG comprises at least one thermocouple provided in or on the substrate; and wherein the first temperature sensor is located proximate to or in contact with the at least one thermocouple of the first TEG.

21. The core temperature sensing system of claim 20, wherein the first temperature sensor is located on or adjacent to one of: a backside of the substrate, and a frontside of a capping layer provided over the at least one thermocouple.

22. A method for determining a core temperature of an object, comprising:

receiving a first heat flux signal from a first heat flux sensor of a first sensor device relating to a measured first heat flux and receiving a first temperature signal from a first temperature sensor of the first sensor device relating to a measured first temperature, the first heat flux sensor being a first thermoelectric generator (TEG) and the first sensor device comprising a first integrated circuit comprising the first TEG;

calculating a core temperature based on the measured first heat flux from the first heat flux signal and the measured first temperature from the first temperature signal:

receiving a second heat flux signal from a second heat flux sensor of a second sensor device relating to a measured second heat flux and receiving a second temperature signal from a second temperature sensor of the second sensor device relating to a measured second temperature, the second heat flux sensor being a second TEG and the second sensor device comprising a second integrated circuit comprising the second TEG; and calculating a core temperature based on the measured first heat flux from the first heat flux signal, the measured first temperature from the first temperature signal, the measured second heat flux from the second heat flux signal and the measured second temperature from the second temperature signal.

23. One or more non-transitory computer readable media having a computer program stored thereon, the computer program comprising computer program code which is configured, when said computer program is run on one or more physical computing devices, to cause said one or more physical computing devices to implement the method of claim 22.

* * * * *